(12) United States Patent
Mitsui et al.

(10) Patent No.: US 6,683,218 B1
(45) Date of Patent: *Jan. 27, 2004

(54) PROCESS FOR PREPARING A TETRAKIS(FLUOROARYL) BORATE DERIVATIVE

(75) Inventors: Hitoshi Mitsui, Nara (JP); Ikuyo Katsumi, Osaka (JP); Naoko Yamamoto, Nishinomiya (JP)

(73) Assignee: Nippon Shokubai Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/955,854

(22) Filed: Oct. 21, 1997

(30) Foreign Application Priority Data

Oct. 25, 1996 (JP) .............................. 8-284170
Oct. 25, 1996 (JP) .............................. 8-284173

(51) Int. Cl.$^7$ ................................. C07F 5/02
(52) U.S. Cl. ....................................... 568/6
(58) Field of Search ..................... 568/1, 3, 6

(56) References Cited

U.S. PATENT DOCUMENTS

| | | | | |
|---|---|---|---|---|
| 5,362,423 A | | 11/1994 | Ikeda et al. ............. | 260/665 R |
| 5,399,780 A | * | 3/1995 | Ikeda ............................ | 568/1 |
| 5,473,036 A | * | 12/1995 | Pitrowski ....................... | 528/4 |
| 5,488,169 A | * | 1/1996 | Ikeda ............................ | 568/3 |
| 5,510,536 A | * | 4/1996 | Ikeda ............................ | 568/6 |
| 5,693,261 A | * | 12/1997 | Krzystowski | |

FOREIGN PATENT DOCUMENTS

| | | |
|---|---|---|
| DE | 43 37 083 A1 | 5/1994 |
| DE | 4337083 A1 | 5/1994 |
| EP | 0604959 A2 | 7/1994 |
| EP | 0 604 961 A2 | 7/1994 |
| EP | 0604961 A2 | 7/1994 |
| EP | 0604963 A1 | 7/1994 |
| EP | 0728760 A2 | 8/1996 |
| EP | 0 728 761 A2 | 8/1996 |
| EP | 0825195 A1 | 2/1998 |
| JP | 6-247 980 A | 9/1994 |
| WO | WO98/22470 | 5/1998 |
| WO | WO98/22475 | 5/1998 |

OTHER PUBLICATIONS

CA:88:89834 abys of CS 169418, Jun. 1974.*
CA:67:43845 abs of "Preparation of ethyl magnesium chloride in hydrocarbon solvent", Smai Chim Ind (Milan), 49(2),pp 142–6, 1967.*
"Processes and Apparatuses of Chemical Technology", A.N. Planovsky et al. Moscow, Goskhimizdat Publishers, 1982, pp. 512–513.

J. L. W. Pohlman et al., "Preparation and Characterization of Group III A Derivatives"; *Zeitschrift Fuer Naturforschung*, Teil B: Anorganische Chemie, vol. 20B, pp. 5–11, (1965).
Robert J. Harper et al., "Reactuins of Organometallics with Fluoroaromatic Compounds", *J. Org. Chem.*, vol. 29, pp. 2385–2389, (1964).

* cited by examiner

Primary Examiner—Jean F. Vollano
(74) Attorney, Agent, or Firm—Kubovcik & Kubovcik

(57) ABSTRACT

A fluoroaryl magnesium derivative expressed by General Formula (1):

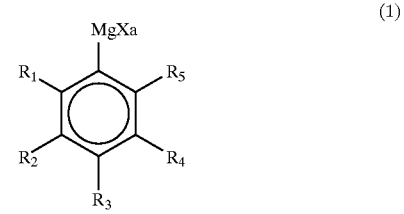

(1)

where each of $R_1$–$R_5$ represents a hydrogen atom, a fluorine atom, a hydrocarbon group, or an alkoxy group while at least one of $R_1$–$R_5$ representing a fluorine atom, and Xa represents a chlorine atom, a bromine atom, or an iodine atom; and boron halide expressed by General Formula (2):

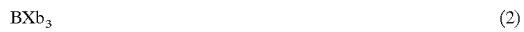

(2)

where Xb represents a fluorine atom, a chlorine atom, a bromine atom, or an iodine atom, are reacted with each other in a solvent (a) containing diethyl ether and/or tetrahydrofuran, after which the resulting reaction solution is added to a solvent (b) having a higher boiling point than diethyl ether and/or tetrahydrofuran while diethyl ether and/or tetrahydrofuran are distilled out. Consequently, it has become possible to obtain a (fluoroaryl)borane compound expressed by General Formula (3):

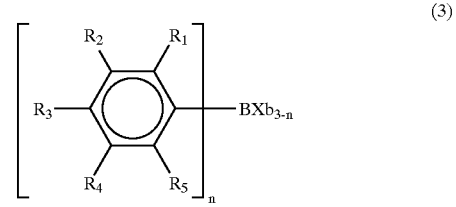

(3)

where each of $R_1$–$R_5$, and Xb, represents the same as above, and n represents 2 or 3, from which magnesium halide produced as a by-product is separated and removed, selectively in a simple manner at a low cost.

19 Claims, No Drawings

PROCESS FOR PREPARING A TETRAKIS(FLUOROARYL) BORATE DERIVATIVE

FIELD OF THE INVENTION

The present invention relates to a process for preparing a (fluoroaryl)borane compound, such as tris(fluoroaryl)borane and bis(fluoroaryl)boryl halide, serving, for example, as a useful cocatalyst for a metallocene catalyst (polymerization catalyst) used in a cation complex polymerization reaction, and to a process for preparing a tetrakis(fluoroaryl)borate derivative.

BACKGROUND OF THE INVENTION

A (fluoroaryl)borane compound, particularly, tris(pentafluorophenyl)borane, is a useful compound as a cocatalyst for promoting the activity of a metallocene catalyst (polymerization catalyst) used in a cation complex polymerization reaction, and recently, the metallocene catalyst has been receiving considerable attention as an olefin polymerization catalyst.

An example process of obtaining the above-mentioned tris(pentafluorophenyl)borane is disclosed in Proc. Chem. Soc., 1963 (July), 212. More specifically, pentafluorophenyl lithium produced by reacting bromopentafluorobenzene and n-butyl lithium (n-BuLi) is reacted with boron trichloride, and as a consequence, tris(pentafluorophenyl)borane is obtained. However, in this process, the reaction system must be cooled to −78° C. which makes this process almost inapplicable to industrial use.

To solve the above problem, a process using the Grignard reaction is disclosed in Z. Naturforsch., 20b, 5 (1965) as another example process of obtaining tris(pentafluorophenyl)borane. According to this process, for example, pentafluorophenyl magnesium bromide and boron trifluoride diethyl etherate are reacted with each other in a chain ether solvent. Thus, it is not necessary to cool the reaction system to −78° C., which makes this process advantageous over the above-mentioned reaction.

Further, Japanese Laid-open Patent Application No. 199871/1994 (Tokukaihei 6-199871) discloses a process of obtaining triarylborane by reacting a aryl magnesium halide derivative and boron halide in a chain ether solvent or a mixed solvent of the chain ether solvent and an aromatic hydrocarbon solvent. The above publication also discloses a process of separating and removing magnesium halide produced as a by-product from the target product, namely triarylborane.

A tetrakis(fluoroaryl)borate derivative is also a useful compound as the above cocatalyst. For example, Japanese Laid-open Patent Application No. 247980/1994 (Tokukaihei 6-247980) discloses a process of producing tetrakis(pentafluorophenyl)borate derivative as one kind of the tetrakis(fluoroaryl)borate derivative. More specifically, a process of reacting a pentafluorophenyl magnesium derivative and boron halide, such as boron trifluoride, or a boron compound, such as tris(pentafluorophenyl)borane is disclosed. When boron halide is used in the above process, magnesium halide is produced as a by-product together with the target product, namely, the tetrakis(pentafluorophenyl)borate derivative.

However, since the above conventional processes use the chain ether solvent having a relatively low boiling point, such as diethyl ether, the reaction system must be cooled. Thus, to produce the (fluoroaryl)borane compound for industrial use, a cooling apparatus or the like is indispensable. Moreover, diethyl ether is highly inflammable. In addition, in the above conventional processes, it is so difficult to control the reaction that a by-product, such as a quaternary compound of boron like a tetrakis(fluoroaryl)borate derivative, is produced. This makes it difficult to selectively obtain the (fluoroaryl)borane compound, such as tris(fluoroaryl)borane and bis(fluoroaryl)boryl halide. Furthermore, the chain ether solvent is generally expensive compared with a cyclic ether solvent.

Thus, the above conventional processes have a problem that they are not readily applied for industrial use, in other words, not only are the solvents hard to handle, but also the (fluoroaryl)borane compound, such as tris(fluoroaryl)borane and bis(fluoroaryl)boryl halide, from which magnesium halide produced as a by-product is separated and removed, can not be produced selectively in a simple manner at a low cost. Using a cyclic ether solvent in the above conventional processes triggers an unwanted side-reaction, such as a ring-opening polymerization of the cyclic ether solvent. In addition, using an aromatic hydrocarbon solvent alone in the above conventional processes reduces the yield of the (fluoroaryl)borane compound, such as tris(fluoroaryl)borane and bis(fluoroaryl)boryl halide.

On the other hand, when magnesium halide remains in the (fluoroaryl)borane compound or tetrakis(fluoroaryl)borate derivative used as the cocatalyst for the metallocene catalyst, the metallocene catalyst loses its activity considerably. Thus, when the above compound or derivative is used as the above cocatalyst, magnesium halide produced as a by-product must be separated and removed.

However, since the tetrakis(pentafluorophenyl)borate derivative and magnesium halide have almost the same solubility into solvents, they can not be isolated easily. In other words, in the above conventional process of producing the tetrakis(fluoroaryl)borate derivative, the by-product, namely magnesium halide, can not be separated and removed easily from the target product, namely the tetrakis(fluoroaryl)borate derivative. Thus, the above conventional process of producing the tetrakis(fluoroaryl)borate derivative has a problem that it can not produce the tetrakis(fluoroaryl)borate derivative from which the by-product, namely, magnesium halide, is separated and removed.

A process for preparing a fluoroaryl magnesium derivative which is an intermediate in the process of preparing the tetrakis(fluoroallyl)borate derivative is disclosed, for example, in J. Org. Chem., 29, 2385 (1964). More specifically, an alkyl magnesium derivative, such as ethyl magnesium bromide (EtMgBr), is dropped to a solution prepared by dissolving pentafluorobenzene into an ether solvent, such as tetrahydrofuran (THF), to trigger an EtMgBr-pentafluorobenzene reaction. Consequently, a pentafluorophenyl magnesium derivative is obtained as one kind of the fluoroaryl magnesium derivative. Japanese Laid-open Patent Application No. 247976/1994 (Tokukaihei 6-247976) discloses another producing process. In this process, the pentafluorophenyl magnesium derivative is obtained by dropping a solution prepared by dissolving pentafluorobenzene into an ether solvent to another solution prepared by mixing an alkyl magnesium derivative with the ether solvent.

In these processes, the pentafluorophenyl magnesium derivative is obtained through an exchange reaction, in which an alkyl group in the alkyl magnesium derivative is replaced with a pentafluorophenyl group.

However, to produce the tetrakis(pentafluorophenyl) borate derivative by the above conventional process, the alkyl magnesium derivative is produced in the first step, the above exchange reaction is carried out in the second step to obtain the pentafluorophenyl magnesium derivative, and the pentafluorophenyl magnesium derivative is reacted with a boron compound in the third step. In other words, since the alkyl magnesium derivative and pentafluorophenyl magnesium derivative are prepared separately before obtaining the tetrakis(pentafluorophenyl)borate derivative, the reaction takes place in three steps. Thus, there is a problem that the above conventional processes cannot produce the tetrakis (pentafluorophenyl)borate derivative effectively in a simple manner.

SUMMARY OF THE INVENTION

Therefore, it is a first object of the present invention to provide a producing process of a (fluoroaryl)borane compound, such as tris(fluoroaryl)borane and bis (fluoroaryl)boryl halide, from which magnesium halide produced as a by-product is separated and removed, selectively in a simple manner at a low cost.

The inventors of the present invention conducted a research diligently on a producing process of the (fluoroaryl) borane compound, and discovered that magnesium halide produced as a by-product with the (fluoroaryl)borane compound precipitates from the reaction system and deposits, and that the (fluoroaryl)borane compound can be produced selectively at a low cost in a simple manner by:

(1) reacting a fluoroaryl magnesium derivative and boron halide in a solvent (a) containing diethyl ether and/or tetrahydrofuran;

(2) adding the resulting reaction solution to a solvent (b) having a higher boiling point than diethyl ether and/or tetrahydrofuran while distilling out diethyl ether and/or tetrahydrofuran. In other words, the inventors discovered that the (fluoroaryl)borane compound, such as tris(fluoroaryl)borane and bis(fluoroaryl)boryl halide, from which magnesium halide produced as a by-product is separated and removed, can be produced selectively in a simple manner at a low cost by adopting the above process.

That is to say, to fulfill the above first object, process for preparing a (fluoroaryl)borane compound of the present invention relates to a process for preparing a (fluoroaryl) borane compound expressed by General Formula (3):

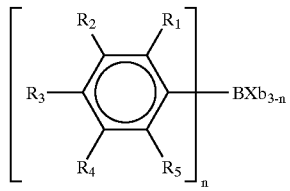

(3)

where each of $R_1$–$R_5$ represents a hydrogen atom, a fluorine atom, a hydrocarbon group, or an alkoxy group while at least one of $R_1$–$R_5$ represents a fluorine atom, Xb represents a fluorine atom, a chlorine atom, a bromine atom, or an iodine atom, and n represents 2 or 3, and the above producing process is characterized by reacting, a fluoroaryl magnesium derivative expressed by General Formula (1):

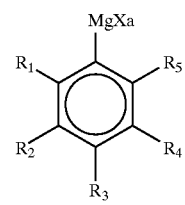

(1)

where each of $R_1$–$R_5$ represents a hydrogen atom, a fluorine atom, a hydrocarbon group, or an alkoxy group while at least one of $R_1$–$R_5$ represents a fluorine atom, Xa represents a chlorine atom, a bromine atom or an iodine atom, with boron halide expressed by General Formula (2):

$$BXb_3 \qquad (2)$$

where Xb represents a fluorine atom, a chlorine atom, a bromine atom, or an iodine atom, in a solvent (a) containing diethyl ether and/or tetrahydrofuran, and then adding a resulting reaction solution to a solvent (b) having a higher boiling point than diethyl ether and/or tetrahydrofuran and distilling out diethyl ether and/or tetrahydrofuran.

Also, to fulfill the above first object, a process for preparing a (fluoroaryl)borane compound of the present invention relates to a process for preparing the (fluoroaryl)borane compound expressed by General Formula (3) above characterized by reacting the fluoroaryl magnesium derivative expressed by General Formula (1) above with boron halide expressed by General Formula (2) above in a solvent (c) containing diethyl ether and/or tetrahydrofuran and a compound having a higher boiling point than diethyl ether and/or tetrahydrofuran, and then distilling out diethyl ether and/or tetrahydrofuran from the resulting reaction solution.

Magnesium halide does not dissolve into solvents (specified below) except for diethyl ether and tetrahydrofuran. In contrast, the (fluoroaryl)borane compound dissolves into solvents including diethyl ether and tetrahydrofuran. In other words, magnesium halide and the (fluoroaryl)borane compound dissolve into solvents except diethyl ether and tetrahydrofuran at different solubilities. Thus, according to the above process, since diethyl ether and/or tetrahydrofuran are distilled out from the reaction system, magnesium halide produced as a by-product together with the (fluoroaryl) borane compound precipitates from the reaction system and deposits. In short, magnesium halide produced as a by-product can be separated and removed. According to the above process, since the reaction can be readily controlled, the solvent (a) is not limited to chain ether solvents. In other words, other kinds of solvents, such as cyclic ether solvents which are relatively easy to handle, can be used. Also, since the resulting (fluoroaryl)borane compound, such as tris (fluoroaryl)borane and bis(fluoroaryl)boryl halide, does not produce a complex nor a quaternary compound, the (fluoroaryl)borane compound can be readily purified. Consequently, it has become possible to produce the (fluoroaryl)borane compound, such as tris(fluoroaryl)borane and bis(fluoroaryl)boryl halide, from which magnesium halide produced as a by-product is separated and removed, selectively in a simple manner at a low cost. Thus, the present process is advantageous over the conventional processes for industrial use, and makes it possible to obtain the (fluoroaryl)borane compound, from which magnesium halide is separated and removed, at high yield and selectivity.

Also, it is a second object of the present invention to provide a process for preparing a tetrakis(fluoroaryl)borate derivative, from which magnesium halide produced as a by-product is separated and removed, in a simple manner at a low cost.

The inventors of the present invention conducted a research diligently on a process for preparing the tetrakis(fluoroaryl)borate derivative, and discovered that the tetrakis(fluoroaryl)borate derivative, from which magnesium halide produced as a by-product is separated and removed, can be produced in a simple manner at a low cost by reacting the (fluoroaryl)borane compound obtained by adopting the above process and a fluoroaryl magnesium derivative, and have achieved the present invention.

To be more specific, to fulfill the above second object, a process for preparing a tetrakis(fluoroaryl)borate derivative of the present invention relates to a process for preparing a tetrakis(fluroraryl)borate derivative expressed by General Formula (5):

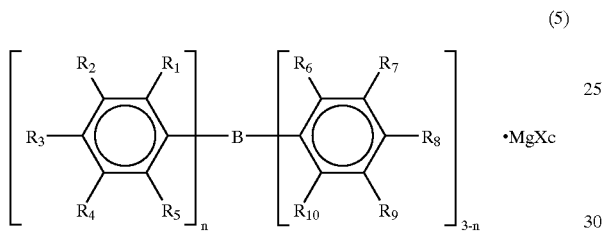

(5)

where each of $R_1$–$R_5$ represents a hydrogen atom, a fluorine atom, a hydrocarbon group, or an alkoxy group while at least one of $R_1$–$R_5$ and one of $R_6$–$R_{10}$ representing a fluorine atom, Xc represents a chlorine atom, a bromine atom, or an iodine atom, and n represents 2 or 3, and the above producing process is characterized by reacting the (fluoroaryl)borane compound obtained by the above process with a fluoroaryl magnesium derivative expressed by General Formula (4):

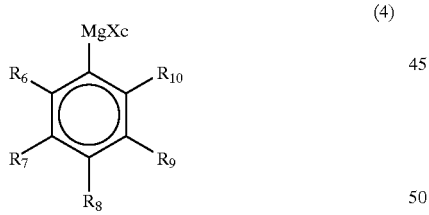

(4)

where each of $R_6$–$R_{10}$ represents a hydrogen atom, a fluorine atom, a hydrocarbon group, or an alkoxy group while at least one of $R_6$–$R_{10}$ represents a fluorine atom, and Xc represents a chlorine atom, a bromine atom or an iodine atom.

According to the above process, it has become possible to produce the tetrakis(fluoroaryl)borate derivative, from which magnesium halide produced as a by-product when producing the (fluoroaryl)borane compound is separated and removed, in a simple manner at a low cost.

Also, to fulfil the above second object, a process for preparing a tetrakis(fluoroaryl)borate derivative of the present invention relates to a process for preparing a tetrakis(fluoroaryl)borate derivative expressed by General Formula (10):

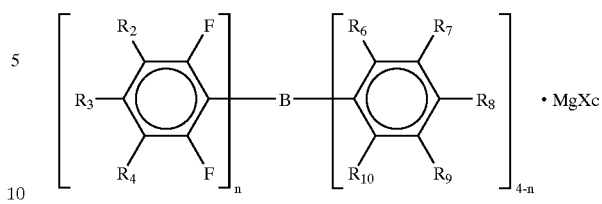

(10)

where each of $R_2$–$R_4$ and $R_6$–$R_{10}$ represents a hydrogen atom, a fluorine atom, a hydrocarbon group, or an alkoxy group while at least one of $R_6$–$R_{10}$ representing a fluorine atom, Xc represents a chlorine atom, a bromine atom, or an iodine atom, and n represents 2 or 3, and the above producing process is characterized by, (A) reacting aryl fluoride expressed by General Formula (6):

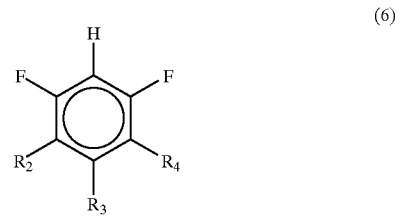

(6)

where each of $R_2$–$R_4$ represents a hydrogen atom, a fluorine atom, a hydrocarbon group, or an alkoxy group, halogenated hydrocarbon expressed by General Formula (7):

$R_0 X a$     (7)

where $R_0$ represents a hydrocarbon group and Xa represents a chlorine atom, a bromine atom, or an iodine atom, and magnesium with one another in a solvent (a) containing diethyl ether and/or tetrahydrofuran to obtain a fluoroaryl magnesium derivative expressed by General Formula (8):

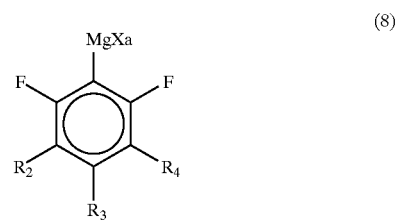

(8)

where each of $R_2$–$R_4$ represents a hydrogen atom, a fluorine atom, a hydrocarbon group, or an alkoxy group, and Xa represents a chlorine atom, a bromine atom, or an iodine atom;

(B) reacting the resulting fluoroaryl magnesium derivative with boron halide expressed by General Formula (2) above;

(C) adding a resulting reaction solution to a solvent (b) having a higher boiling point than diethyl ether and/or tetrahydrofuran, (D) distilling out diethyl ether and/or tetrahydrofuran to obtain a (fluoroaryl)borane compound expressed by General Formula (9):

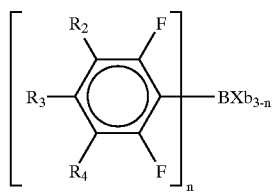

(9)

where each of $R_2$–$R_4$ represents a hydrogen atom, a fluorine atom, a hydrocarbon group, or an alkoxy group, Xb represents a fluorine atom, a chlorine atom, a bromine atom, or an iodine atom, and n represents 2 or 3, and (E) reacting the resulting (fluoroaryl)borane compound with the fluoroaryl magnesium derivative expressed by General Formula (4) above.

According to the above process, it has become possible to produce the tetrakis(fluoroaryl)borate derivative, from which magnesium halide produced as a by-product is separated and removed, in a simple manner at a low cost using aryl fluoride as a starting material.

Further, it is a third object of the present invention to provide a process for preparing a tetrakis(fluoroaryl)borate derivative effectively in a simple manner at a low cost virtually in a single step (so-called 1 pot) reaction.

The inventors of the present invention conducted a research diligently on a process for preparing the tetrakis (fluoroaryl)borate derivative, and discovered that the tetrakis (fluoroaryl)borate derivative can be produced effectively in a simple manner at a low cost by reacting aryl fluoride, halogenated hydrocarbon, and magnesium in an ether solvent (e) or a mixed solvent of the ether solvent (e) and a hydrocarbon solvent to obtain a fluoroaryl magnesium derivative, and subsequently reacting the resulting fluoroaryl magnesium derivative and boron halide or tris(fluoroaryl) borane virtually in a single step (so-called 1 pot) reaction, and have achieved the present invention.

To be more specific, to fulfil the third object of the present invention, a producing process of a tetrakis(fluoroaryl) borate derivative of the present invention relates to a process for preparing a tetrakis(fluoroaryl)borate derivative expressed by General Formula (11):

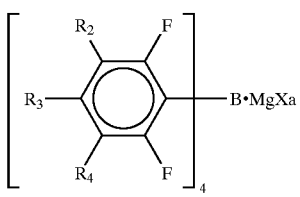

(11)

where each of $R_2$–$R_4$ represents a hydrogen atom, a fluorine atom, a hydrocarbon group, or an alkoxy group, and Xa represents a chlorine atom, a bromine atom or an iodine atom, and the above producing process is characterized by reacting aryl fluoride expressed by General Formula (6) above, halogenated hydrocarbon expressed by General Formula (7) above, and magnesium with one another in the ether solvent (e) or a mixed solvent of the ether solvent (e) and hydrocarbon solvent to obtain the fluoroaryl magnesium derivative expressed by General Formula (8) above, and then reacting the resulting fluoroaryl magnesium derivative and boron halide expressed by General Formula (2) above.

According to the above process, the reaction can take place virtually in a single step, thereby making it possible to produce the tetrakis(fluoroaryl)borate derivative effectively in a simple manner at a low cost.

Also, to fulfill the third object, a process for preparing a tetrakis(fluoroaryl)borate derivative of the present invention relates to a process for preparing a tetrakis(fluoroaryl)borate derivative expressed by General Formula (13):

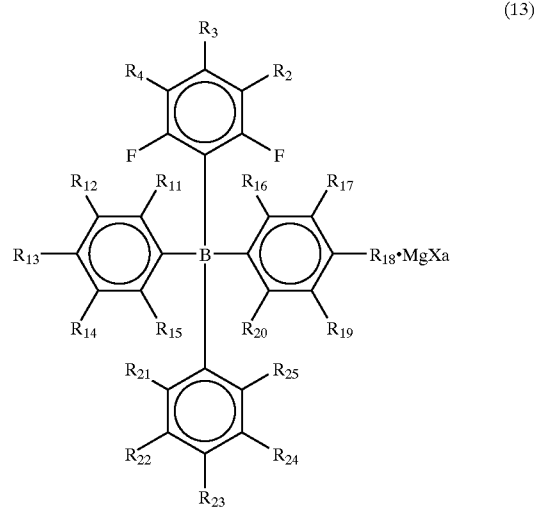

(13)

where each of $R_2$–$R_4$ and $R_{11}$–$R_{25}$ represents a hydrogen atom, a fluorine atom, a hydrocarbon group, or an alkoxy group while at least one of $R_{11}$–$R_{25}$ represents a fluorine atom, and Xa represents a chlorine atom, a bromine atom, or an iodine atom, and the above process is characterized by, (A) reacting aryl fluoride expressed by General Formula (6) above, halogenated hydrocarbon expressed by General Formula (7) above, and magnesium with one another in the ether solvent (e) or mixed solvent of the ether solvent (e) and hydrocarbon solvent to obtain the fluoroaryl magnesium derivative expressed by General Formula (8) above; and (B) reacting the resulting fluoroaryl magnesium derivative with tris(fluoroaryl)borane expressed by General Formula (12):

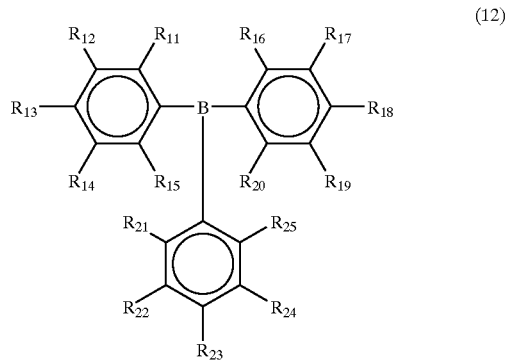

(12)

where each of $R_{11}$–$R_{25}$ represents a hydrogen atom, a fluorine atom, a hydrocarbon group or an alkoxy group while at least one of $R_{11}$–$R_{25}$ represents a fluorine atom.

According to the above process, the reaction can take place virtually in a single step, thereby making it possible to produce the tetrakis(fluoroaryl)borate derivative effectively in a simple manner at a low cost. Further, according to the above process, it has become possible to produce a tetrakis (fluoraryl)borate derivative, in which at least one of four fluoroaryl groups bonded to a boron atom has a different structure from the other fluoroaryl groups.

Further objects, the nature and advantages of the invention will be understood by the following description. Also, the effects of the present invention will be explained clearly in the following description.

DESCRIPTION OF THE EMBODIMENTS

A process for preparing the (fluoroaryl)borane compound expressed by General Formula (3) above is a process of reacting the fluoroaryl magnesium derivative expressed by General Formula (1) above (hereinafter, referred to as the fluoroaryl magnesium derivative (1)) and boron halide expressed by General Formula (2) above (hereinafter, referred to as boron halide (2)) in the solvent (a) containing diethyl ether and/or tetrahydrofuran, and subsequently adding the resulting reaction solution to the solvent (b) having a higher boiling point than diethyl ether (boiling point: 34.48° C.) and/or tetrahydrofuran (boiling point: 66° C.) while distilling out diethyl ether and/or tetrahydrofuran Also, a process for preparing the (fluoroaryl)borane compound expressed by General Formula (3) above is a process of reacting the fluoroaryl magnesium derivative (1) and boron halide (2) in the solvent (c) containing diethyl ether and/or tetrahydrofuran and a compound having a higher boiling point than diethyl ether and/or tetrahydrofuran, and subsequently distilling out diethyl ether and/or tetrahydrofuran from the resulting reaction solution.

Further, a process for preparing the tetrakis(fluoroaryl) borate derivative expressed by General Formula (5) is a process of reacting the (fluoroaryl)borane compound obtained by the above process and the fluoroaryl magnesium derivative expressed by General Formula (4) above (hereinafter, referred to as the fluoroaryl magnesium derivative (4)).

Furthermore, a process for preparing the tetrakis (fluoroaryl)borate derivative expressed by General Formula (10) above is a process of:

(A) reacting aryl fluoride expressed by General Formula (6) above (hereinafter, referred to as aryl fluoride (6)), halogenated hydrocarbon expressed by General Formula (7) above (hereinafter, referred to as halogenated hydrocarbon (7)), and magnesium in the solvent (a) containing diethyl ether and/or tetrahydrofuran to obtain the fluoroaryl magnesium derivative expressed by General Formula (8) above (hereinafter, referred to as the fluoroaryl magnesium derivative (8));

(B) reacting the resulting fluoroaryl magnesium derivative (8) and boron halide (2);

(C) adding the resulting reaction solution to the solvent (b) having a higher boiling point than diethyl ether and/or tetrahydrofuran while distilling out diethyl ether and/or tetrahydrofuran to obtain the (fluoroaryl)borane compound expressed by General Formula (9); and (D) reacting the resulting (fluoroaryl)borane compound and the fluoroaryl magnesium derivative (4).

In the present invention, the fluoroaryl magnesium derivative (1) used as a starting material is a compound, in which each of the substituent groups denoted as $R_1$–$R_5$ is a hydrogen atom, a fluorine atom, a hydrocarbon group, or an alkoxy group while at least one of $R_1$–$R_5$ is a fluorine atom, and a substituent group denoted as Xa is a chlorine atom, a bromine atom, or an iodine atom.

Also, the fluoroaryl magnesium derivative (4) used in the present invention is a compound, in which each of substituent groups denoted as $R_6$–$R_{10}$ is a hydrocarbon atom, a fluorine atom, a hydrocarbon group, or an alkoxy group while at least one of $R_6$–$R_{10}$ is a fluorine atom, and a substituent group denoted as Xc is a chlorine atom, a bromine atom, or an iodine atom.

The hydrocarbon group referred to herein means an aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the reactions taking place in the present invention. Examples of such a functional group are: a methoxy group, a methylthio group, an N,N-dimethylamino group, an o-anise group, a p-anise group, a trimethylsilyl group, a t-butyldimethylsilyloxy group, a trifluoromethyl group, etc.

The alkoxy group is expressed by General Formula (A):

$$-OR_a \qquad (A)$$

where $R_a$ represents a hydrocarbon group. Examples of the hydrocarbon group denoted as $R_a$ in the formula are: an aryl group, a straight-chain, branched-chain, or cyclic alkyl group having up to 12 carbon atoms, a straight-chain, branched-chain, or cyclic alkenyl group having 2–12 carbon atoms. The hydrocarbon group may further include a functional group that remains inactive to the reaction taking place in the present invention.

Examples of the alkoxy group expressed by General Formula (A) above are: a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, a phenoxy group, etc.

Examples of the fluoroaryl magnesium derivatives (1) and (4) are: pentafluorophenyl magnesium chloride, pentafluorophenyl magnesium bromide, pentafluorophenyl magnesium iodide, 1,2,3,5-tetrafluorophenyl magnesium bromide, 1,2,4,5-tetrafluorophenyl magnesium chloride, 1,2,4-trifluorophenyl magnesium bromide, 1,3,5-trifluorophenyl magnesium iodide, 2,3,5,6-tetrafluoro-4-methylphenyl magnesium bromide, 2,5-difluorophenyl magnesium bromide, 2,5-difluoro-3-methylphenyl magnesium chloride, 2,3,4,6-tetrafluoro-5-methylphenyl magnesium bromide, 2,4,6-trifluoro-5-methylphenyl magnesium chloride, 2,3,5,6-tetrafluoro-4-methoxyphenyl magnesium bromide, 2,3,6-trifluoro-5-methoxyphenyl magnesium chloride, 2,4,6-trifluoro-5-methoxyphenyl magnesium bromide, 2,5-difluoro-3-methoxyphenyl magnesium chloride, 2,5-difluoro-4-methoxyphenyl magnesium bromide, 2-fluorophenyl magnesium bromide, 4-fluorophenyl magnesium bromide, 2-fluoro-4-methylphenyl magnesium bromide, etc. Of all these example fluoroaryl magnesium derivatives, the most preferred is pentafluorophenyl magnesium bromide. More than one kind of the fluoroaryl magnesium derivatives (1) and (4) can be used as occasion demands.

A producing process of the fluoroaryl magnesium derivatives (1) and (4) is not especially limited. For example, the fluoroaryl magnesium derivatives (1) and (4) can be obtained by a reaction of magnesium and fluoroaryl halide, such as fluoroaryl chlorides, fluoroaryl bromide, and fluoroaryl iodide.

The fluoroaryl magnesium derivative expressed by General Formula (1) above, in which at least two substituent groups denoted as $R_1$ and $R_5$ are fluorine atoms, that is, the fluoroaryl magnesium derivative (8), can be obtained by reacting: aryl fluoride having fluorine atoms at least at two positions (ortho-positions) neighboring to a hydrogen atom, that is, aryl fluoride (6); hydrocarbon halide (7); and magnesium. A producing process of the tetrakis(fluoroaryl)borate derivative using aryl fluoride (6) as the starting material will be explained below.

Boron halide (2) is a compound whose substituent group denoted as Xb is a fluorine atom, a chlorine atom, a bromine atom, or an iodine atom. Examples of boron halide (2) are boron trifluoride, boron trichloride, boron tribromide, and boron triiodide. Of all these examples, the most preferred is boron trifluoride. More than one kind of boron halide (2) can be used as occasion demands. Alternatively, boron halide (2) may form an ether complex, such as a diethyl ether complex and a tetrahydrofuran complex.

The solvent (a) referred to herein is not especially limited as long as it is a non-aqueous solvent that remains inactive to the reactions taking place in the present invention while containing diethyl ether and/or tetrahydrofuran, and into which the fluoroaryl magnesium derivatives (1) and (8), boron halide (2), the (fluoroaryl)borane compound as the target product, such as tris(fluoroaryl)borane and bis(fluoroaryl)boryl halide, and optionally aryl fluoride (6) and halogenated hydrocarbon (7), can dissolve.

The solvent (b) referred to herein is not especially limited as long as it is a non-aqueous solvent that remains inactive to the reactions taking place in the present invention while having a higher boiling point than diethyl ether and/or tetrahydrofuran, and into which the (fluoroaryl)borane compound as the target product can dissolve but magnesium halide produced as a by-product can not.

The solvent (c) referred to herein is not especially limited as long as it is a non-aqueous solvent that remains inactive to the reactions taking place in the present invention while containing diethyl ether and/or tetrahydrofuran and a compound having a higher boiling point than diethyl ether and/or tetrahydrofuran, and into which the fluoroaryl magnesium derivative (1), boron halide (2), and the (fluoroaryl)borane compound as the target product can dissolve but magnesium halide produced as a by-product can not.

The solvent (d) referred to herein is not especially limited as long as it is a non-aqueous solvent that remains inactive to the reactions taking place in the present invention while containing diethyl ether and/or tetrahydrofuran and a compound having a higher boiling point than diethyl ether and/or tetrahydrofuran, and into which the (fluoroaryl)borane compound, fluoroaryl magnesium derivative (4), and the tetrakis(fluoroaryl)borate derivative as the target product can dissolve but magnesium halide produced as a by-product can not.

When both diethyl ether and tetrahydrofuran are used in the solvent (a), (c), or (d), a ratio of these two substances is not especially limited. Also, an ether solvent and a hydrocarbon solvent are preferable as the compound contained in the solvent (b), (c), or (d). The solvent (a) may contain both the ether solvent and hydrocarbon solvent (hereinafter, which are collectively referred to as the ether and hydrocarbon solvent) as occasion demands.

Examples of the ether solvent include, but are not limited to:
  chain ethers, such as di-n-propyl ether, diisopropyl ether, di-n-butyl ether, diisobutyl ether, di-n-pentyl ether, diisopentyl ether, 1,2-dimethoxy ethane, 1,2-diethoxy ethane, and di(2-methoxyethyl)ether;
  cyclic ethers, such as tetrahydropyran, and 1,4-dioxane; etc.

Note that the ether solvent does not include diethyl ether and tetrahydrofuran, and hereinafter, the ether solvent, diethyl ether, and tetrahydrofuran are collectively referred to as the ether solvent (e).

Examples of the hydrocarbon solvent include, but are not limited to:
  straight-chain, branched-chain, or cyclic aliphatic hydrocarbons, such as n-pentane, isopentane, hexane, cyclohexane, heptane, octane, nonane, decane, undecane, dodecane, tridecane, tetradecane, pentadecane, hexadecane, octadecane, paraffin, and petroleum ether;
  aromatic hydrocarbons, such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, and butylbenzene; etc.

Examples of the ether and hydrocarbon solvent which can be suitably combined with diethyl ether are: hexane, cyclohexane, heptane, octane, IsoparE of Exxon Corp. (a mixture of isoparaffins having approximately 10 carbon atoms), decane, octadecane, fluid paraffin, etc. Also, examples of the ether and hydrocarbon solvent which can be suitably combined with tetrahydrofuran are: heptane, octane, IsoparE, decane, octadecane, fluid paraffin, etc.

One member or a mixture of two or more members selected from these examples of ether and hydrocarbon solvents can be used effectively. In the producing processes of the present invention, cyclic ether can be used as the ether and hydrocarbon solvent. It is preferable that the ether and hydrocarbon solvent has a boiling point of 60° C. or above, and when being used as the solvent (b), 80° C. or above. In other words, it is preferable to heat the solvent (b) to 80° C. or above, so that diethyl ether and/or tetrahydrofuran can be distilled out quickly. When the ether and hydrocarbon solvent is a mixture, the boiling point means the lowest boiling point of all the mixed compounds. It is preferable that diethyl ether and tetrahydrofuran as well as the ether and hydrocarbon solvent do not form any azeotropic composition.

A ratio of diethyl ether and/or tetrahydrofuran with respect to the ether and hydrocarbon solvent in the solvents (c) and (d) is not especially limited as long as these solvents are made into a homogeneously mixed solvent. However, the ratio is preferably in a range between 1:0 and 1:10 in volume. In short, the ether and hydrocarbon solvent can be used in an amount within an extent that does not give any adverse effect to the reactions taking place in the present invention. Likewise, when the solvent (a) contains the ether and hydrocarbon solvent, the ether and hydrocarbon solvent can be used in an amount within an extent that does not give any adverse effect to the reactions taking place in the present invention.

An amount of the solvent (a) is not especially limited. For example, an amount in which the concentration of the fluoroaryl magnesium derivatives (1) and (8), or boron halide (2) is in a range between 0.1 and 80 percent by weight is preferable. A method of dissolving the fluoroaryl magnesium derivative (1), and either boron halide (2), or both aryl fluoride (6) and halogenated hydrocarbon (7) into the solvent (a) is not especially limited. In other words, a method of preparing a solution by dissolving the fluoroaryl magnesium derivative (1) into the solvent (a), a method of preparing a solution by dissolving boron halide (2) into the solvent (a) as occasion demands, and a method of preparing a solution by dissolving aryl fluoride (6) and halogenated hydrocarbon (7) into the solvent (a) are not especially limited.

An amount of the solvent (b) is not especially limited, and any amount of the solvent (b) can be used as long as the (fluoroaryl)borane compound or tetrakis(fluoroaryl)borate derivative can fully dissolve into the same.

An amount of the solvent (c) is not especially limited. For example, an amount in which the concentration of the fluoroaryl magnesium derivative (1) or boron halide (2) is in a range between 0.1 and 80 percent by weight is preferable. A method of dissolving the fluoroaryl magnesium derivative (1) or boron halide (2) into the solvent (c) is not especially limited. In other words, a method of preparing a solution by dissolving the fluoroaryl magnesium derivative (1) into the solvent (c), and a method of preparing a solution by dissolving boron halide (2) into the solvent (c) as occasion demands are not especially limited.

An amount of the solvent (d) is not especially limited. For example, an amount in which the concentration of the (fluoroaryl)borane compound, or the fluoroaryl magnesium derivative (4) is in a range between 0.1 and 80 percent by weight is preferable. A method of dissolving the (fluoroaryl)borane compound or fluoroaryl magnesium derivative (4) into the solvent (d) is not especially limited. In other words, a method of preparing a solution by dissolving the (fluoroaryl)borane compound or fluoroaryl magnesium derivative (4) into the solvent (d) is not especially limited. Also, the solution obtained by dissolving the (fluoroaryl)borane compound into the solvent (d) may be a solution of the (fluoroaryl)borane compound prepared using the solvents (a), (b), or (c), namely, the reaction solution.

A mole ratio of the fluoroaryl magnesium derivative (1) and boron halide (2) (fluoroaryl magnesium derivative (1)/boron halide (2)) is not especially limited. However, the ratio is preferably in a range between 1.0 and 5.0. Narrowing the range to 2.5 and 5.0 inclusive, more preferably to 2.7 and 4.0 inclusive, and most preferably to 2.8 and 3.5 inclusive, makes it possible to selectively obtain the (fluoroaryl)borane compound expressed by General Formula (3) above whose n is 3, namely, tris(fluoroaryl)borane. Also, narrowing the mole ratio to a range between 1.0 inclusive and 2.5 exclusive, more preferably to a range between 1.2 and 2.4 inclusive, and most preferably to a range between 1.3 and 2.3 inclusive, makes it possible to produce the (fluoroaryl)borane compound expressed by General Formula (3) above whose n is 2, namely, bis(fluoroaryl)boryl halide, as a main product. When the mole ratio is less than 1.0, there remains too much unreacted boron halide (2). On the other hand, when the mole ratio is greater than 5.0, there remains too much unreacted fluoroaryl magnesium derivative (1). Thus, the (fluoroaryl)borane compound, such as tris(fluoroaryl)borane and bis(fluoroaryl)boryl halide, may not be produced effectively.

A method of mixing a solution prepared by dissolving the fluoroaryl magnesium derivative (1) into the solvent (a) or (c) (which is referred to as the solution of the magnesium derivative (1), hereinafter), and another solution prepared by dissolving boron halide (2) into the solvent (a) or (c) is not especially limited. However, it is preferable to drop either solution to the other continuously or sequentially. Here, boron halide (2) may be mixed with the solution of the magnesium derivative (1) directly by skipping the preparation of the solution of boron halide (2).

A mixing temperature of the solution of the magnesium derivative (1) and the solution of boron halide (2) is preferably 80° C. or below, more preferably in a range between −40° C. and 70° C., and most preferably in a range between −20° C. and 50° C. When the above two kinds of solutions are mixed with each other at or below 80° C., a side reaction can be suppressed. If the mixing temperature exceeds 80° C., it becomes difficult to suppress side reactions, thereby reducing the yield and selectivity of the (fluoroaryl)borane compound, such as tris(fluoroaryl)borane and bis (fluoroaryl)boryl halide. Setting the mixing temperature below −40° C. does not attain significant effects compared with a case where the mixing temperature is set within the above range.

While the solution of the magnesium derivative (1) and the solution of boron halide (2) are mixed with each other and stirred, the reaction between the fluoroaryl magnesium derivative (1) and boron halide (2) proceeds in the solvent (a) or (c). If there is water in the reaction system while the reaction is taking place, the fluoroaryl magnesium derivative (1) decomposes by reacting with water. Thus, it is preferable that the above reaction takes place under an inert gas atmosphere, such as a nitrogen gas. Also, it is preferable to displace the air inside the reaction system, namely, a reaction vessel, by an inert gas, such as a nitrogen gas.

Further, it is preferable that the solvent (a) or (c) and boron halide (2) do not contain water. A desiccating method of the solvent (a) or (c) and boron halide (2) is not especially limited.

A reaction temperature is preferably in a range between 30° C. and a reflux temperature of the solvent inclusive, more preferably in a range between 30° C. and 200° C., and most preferably in a range between 30° C. and 70° C. Setting the reaction temperature below 30° C. is not preferable, because the reaction proceeds too slow to produce the (fluoroaryl)borane compound effectively. On the other hand, when the reaction temperature exceeds the reflux temperature of the solvent, it becomes hard to control the reaction.

A reaction time can be set arbitrarily to complete the reaction depending on the reaction temperature, a combination of the fluoroaryl magnesium derivative (1) and boron halide (2), a used amount of them, etc. A reaction pressure is not especially limited either, and the reaction can take place under a normal (ambient), reduced, or increased pressure.

A reaction solution containing the (fluoroaryl)borane compound expressed by General Formula (3) above can be obtained by reacting the fluoroaryl magnesium derivative (1) and boron halide (2) in accordance with the above process. When the reaction solution is obtained using the solvent (a), the reaction solution is added to the solvent (b) while diethyl ether and/or tetrahydrofuran are distilled out from the reaction solution. When the reaction solution is obtained using the solvent (c), diethyl ether and/or tetrahydrofuran are distilled out from the reaction solution. Note that magnesium halide expressed by General Formula (B):

$$MgXaXb \qquad (B)$$

where Xa represents a chlorine atom, a bromine atom, or an iodine atom, and Xb represents a fluorine atom, a chlorine atom, a bromine atom, or an iodine atom, is produced as a by-product together with the (fluoroaryl)borane compound and dissolves into the reaction solution.

An amount of the solvent (b) with respect to the above reaction solution is not especially limited, and any amount can be used as long as the (fluoroaryl)borane compound can fully dissolve into the same, in other words, as long as the (fluoroaryl)borane compound can be obtained in the form of solution after diethyl ether and/or tetrahydrofuran are distilled out from a mixture of the solvent (b) and reaction solution.

A method of adding the reaction solution obtained using the solvent (a) to the solvent (b) is not especially limited.

However, it is preferable to drop the above reaction solution continuously or sequentially to the solvent (b) heated to 80° C. or above. Note that the temperature of the reaction solution is not especially limited as long as it is below the boiling point of diethyl ether or tetrahydrofuran.

Magnesium halide produced as a by-product together with the (fluoroaryl)borane compound dissolves into diethyl ether and tetrahydrofuran, but does not dissolve into the other kinds of solvents (namely, the aforementioned ether solvents and hydrocarbon solvents). In contrast, the (fluoroaryl) borane compound dissolves into diethyl ether and tetrahydrofuran as well as the other kinds of solvents (namely, the ether solvent and hydrocarbon solvent). In other words, magnesium halide and the (fluoroaryl)borane compound dissolve into the other kinds of solvents at different solubilities. Thus, when the reaction solution is added to the solvent (b) heated to 80° C. or above, diethyl ether and/or tetrahydrofuran boil quickly. Consequently, not only diethyl ether and/or tetrahydrofuran are distilled out from the resulting mixture, but also magnesium halide precipitates therefrom and deposits. Magnesium halide precipitates and deposits in a form which can be filtered relatively easy. Therefore, magnesium halide produced as a by-product can be separated and removed from the reaction system by filtering the resulting mixture after diethyl ether and/or tetrahydrofuran are distilled out. However, a method of separating and removing magnesium halide is not limited to the filtration.

A method (timing) of distilling out diethyl ether and/or tetrahydrofuran is not especially limited. However, it is preferable to distill out diethyl ether and/or tetrahydrofuran as quickly as possible for the aforementioned reason. Thus, the most preferred method for the distilling-out is to carry out the distilling-out while adding the reaction solution to the solvent (b) (the addition and distilling-out are carried out concurrently). On the other hand, when diethyl ether and/or tetrahydrofuran are distilled out from the reaction solution obtained using the solvent (c), the reaction solution is heated to 80° C. or above as quickly as possible. Diethyl ether and/or tetrahydrofuran are distilled out under a normal, reduced, or increased pressure. It is preferable to carry out the above addition and distilling-out under an inert gas atmosphere, such as a nitrogen gas.

According to the above process, it has become possible to obtain the (fluoroaryl)borane compound expressed by General Formula (3) above (hereinafter, referred to as the (fluoroaryl)borane compound (3)), in other words, the (fluoroaryl)borane compound (3), such as tris(fluoroaryl) borane and bis(fluoroaryl)boryl halide, from which magnesium halide produced as a by-product is separated and removed. The (fluoroaryl)borane compound (3), particularly tris(pentafluorophenyl)borane, are useful, for example, as a cocatalyst for promoting the activity of metallocene catalysts (polymerization catalyst). Further, when the fluoroaryl magnesium derivative (1) is pentafluorophenyl magnesium bromide, a (pentafluorophenyl)borane compound, such as tris(pentafluorophenyl)borane and bis(pentafluorophenyl) boryl halide, from which magnesium halide produced as a by-product is separated and removed, can be produced effectively in a simpler manner at a low cost. If diethyl ether or tetrahydrofuran remains in the (fluoroaryl)borane compound (3), the activity of the (fluoroaryl)borane compound (3) as a cocatalyst deteriorates. For this reason, it is preferable to distill out substantially the whole amount of diethyl ether and tetrahydrofuran.

Next, a reaction solution containing the tetrakis (fluoroaryl)borate derivative expressed by General Formula (5) above (hereinafter, referred to as the tetrakis(fluoroaryl) borate derivative (5)) is obtained by reacting the above (fluoroaryl)borane compound (3), from which magnesium halide is separated and removed, and the fluoroaryl magnesium derivative (4). It is preferable that the fluoroaryl magnesium derivative (4) is in the form of a solution by being dissolved into diethyl ether and/or tetrahydrofuran, or the solvent (d) (hereinafter, the resulting solution is referred to as the solution of the magnesium derivative (4)). A concentration of the fluoroaryl magnesium derivative (4) in the solution is not especially limited.

A mole ratio of the (fluoroaryl)borane compound (3) and fluoroaryl magnesium derivative (4) ((fluoroaryl)borane compound (3)/fluoroaryl magnesium derivative (4)) is not especially limited. However, a mole ratio near the theoretical ratio, that is, 1.0, is preferable. When the mole ratio is far larger or smaller than 1.0, the tetrakis(fluoroaryl)borate derivative (5) can not be produced effectively.

A method of mixing the solution of the (fluoroaryl)borane compound (3) and the solution of the magnesium derivative (4) is not especially limited. Both kinds of solutions may be mixed at one time, or either solution may be dropped to the other continuously or sequentially.

A mixing temperature of the solution of the (fluoroaryl) borane compound (3) and the solution of the magnesium derivative (4) is not especially limited. However, it is preferable to adjust the mixing temperature to a range between −20° C. and a reflux temperature of the solvent inclusive, more preferably to a range between −20° C. and 100° C., and most preferably to a range between 20° C. and 70° C. The reaction can be controlled more easily by mixing both kinds of solvents within the above temperature range. Adjusting the mixing temperature below −20° C. does not attain significant effects, and therefore, is disadvantageous for industrial use compared with a case where the mixing temperature is adjusted in the above temperature range. On the other hand, when the mixing temperature exceeds the reflux temperature of the solvent, it becomes difficult to control the reaction.

When the solution of the (fluoroaryl)borane compound (3) and the solution of the magnesium derivative (4) are mixed with each other and stirred, the (fluoroaryl)borane compound (3) and magnesium derivative (4) start to react with each other in the resulting solution. If there is water in the reaction system while the reaction is taking place, the fluoroaryl magnesium derivative (4) decomposes by reacting with water. Thus, it is preferable that the above reaction takes place under an inert gas atmosphere, such as a nitrogen gas. Also, it is preferable to displace the air inside the reaction system, namely, a reaction vessel, by an inert gas, such as a nitrogen gas when both kinds of solutions are mixed with each other. A desiccating method of the solution of the magnesium derivative (4) is not especially limited.

A reaction temperature is adjusted to be in a range between 30° C. and the reflux temperature of the solvent inclusive, more preferably in a range between 50° C. and the reflux temperature of the solvent inclusive, and most preferably in a range between 60° C. and the reflux temperature of the solvent inclusive. Adjusting the reaction temperature below 30° C. is not preferable, because the reaction takes place too slow to produce the tetrakis(fluoroaryl)borate derivative (5) effectively. On the other hand, when the reaction temperature exceeds the reflux temperature of the solvent, it becomes difficult to control the reaction.

A reaction time can be set arbitrarily to complete the reaction depending on the reaction temperature, a combination of the (fluoroaryl)borane compound (3) and fluoroaryl magnesium derivative (4), a used amount of them, etc. A reaction pressure is not especially limited either, and the reaction can take place under a normal (ambient), reduced, or increased pressure.

As a result of the above process, a reaction solution containing the tetrakis(fluoroaryl)borate derivative (5) is obtained. When the (fluoroaryl)borane compound (3) is bis(fluoroaryl)boryl halide, magnesium halide expressed by General Formula (C):

$$MgX_bX_c \quad (C)$$

where Xb represents a fluorine atom, a chlorine atom, a bromine atom, or an iodine atom, and Xc represents a chlorine atom, a bromine atom, or an iodine atom, is produced as a by-product together with the tetrakis (fluoroaryl)borate derivative (5) and dissolves into the reaction solution. Thus, to separate and remove magnesium halide from the reaction solution, diethyl ether and/or tetrahydrofuran in the reaction solution are distilled out. On the other hand, when the (fluoroaryl)borane compound (3) is tris(fluoroaryl)borane, diethyl ether and/or tetrahydrofuran in the reaction solution are distilled out as occasion demands.

As a result of the above process, the tetrakis(fluoroaryl) borate derivative (5), from which magnesium halide produced as a by-product is separated and removed, is obtained. The tetrakis(fluoroaryl)borate derivative (5) is a relatively stable compound, and according to the above process, the tetrakis(fluoroaryl)borate derivative (5) can be isolated from the reaction solution in the form of crystals or a solution.

In other words, according to the above process, after the (fluoroaryl)borane compound (3) and fluoroaryl magnesium derivative (4) are reacted with each other in the solvent (d), diethyl ether and/or tetrahydrofuran are distilled out from the reaction system. Thus, for example, when the (fluoroaryl)borane compound (3) is bis(fluoroaryl)boryl halide, magnesium halide produced as a by-product together with the tetrakis(fluoroaryl)borate derivative (5) precipitates from the reaction system and deposits. In short, magnesium halide produced as a by-product can be separated and removed. Consequently, it has become possible to produce the tetrakis(fluoroaryl)borate derivative (5), from which magnesium halide produced as a by-product is separated and removed, in a simple manner at a low cost. Also, the tetrakis(fluoroaryl)borate derivative (5) thus obtained is a relatively stable compound, and according to the above process, the tetrakis(fluoroaryl)borate derivative (5) can be isolated from the reaction solution in the form of crystals or a solution. When the (fluoroaryl)borane compound (3) is tris(fluoroaryl)borane, the tetrakis(fluoroaryl)borate derivative (5) can also be isolated from the reaction solution in the form of crystals or a solution.

Next, a producing process of the tetrakis(fluoroaryl)borate derivative expressed by General Formula (10) above (hereinafter, referred to as the tetrakis(fluoroaryl)borate derivative (10)) using aryl fluoride (6) as a starting material will be explained.

Examples of aryl fluoride (6) are: pentafluorobenzene, 1,2,3,5-tetrafluorobenzene, 1,2,4,5-tetrafluorobenzene, 1,2,4-trifluorobenzene, 1,3,5-trifluorobenzene, 1,3-difluorobenzene, 2,3,5,6-tetrafluorotoluene, 2,3,4,6-tetrafluorotoluene, 2,3,5-trifluorotoluene, 2,4,6-trifluorotoluene, 2,4-difluorotoluene, 2,3,5,6-tetrafluoroanisole, 2,3,4,6-tetrafluoroanisole, 2,4,5-trifluoroanisole, 2,4,6-trifluoroanisole, 2,4-difluoroanisole, 3,5-difluoroanisole, etc.

Halogenated hydrocarbon (7) is a compound, in which the substituent group denoted as $R_0$ is a hydrocarbon group, and the substituent group denoted as Xa is a chlorine atom, a bromine atom, or an iodine atom. Examples of the hydrocarbon group are: an aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the reaction taking place in the present invention. Examples of such a functional group are: a methoxy group, a methylthio group, an N,N-dimethylamino group, an o-anise group, a p-anise group, a trimethylsilyl group, a t-butyldimethylsilyloxy group, a trifluoromethyl group, etc.

Examples of halogenated hydrocarbon (7) are: methyl chloride, methyl bromide, methyl iodide, ethyl chloride, ethyl bromide, ethyl iodide, n-propyl chloride, n-propyl bromide, n-propyl iodide, isopropyl chloride, isopropyl bromide, isopropyl iodide, n-butyl chloride, n-butyl bromide, n-butyl iodide, isobutyl chloride, isobutyl bromide, isobutyl iodide, sec-butyl chloride, sec-butyl bromide, sec-butyl iodide, t-butyl chloride, t-butyl bromide, t-butyl iodide, hexyl chloride, hexyl bromide, hexyl iodide, cyclohexyl chloride, cyclohexyl bromide, cyclohexyl iodide, allyl chloride, allyl bromide, allyl iodide, chlorobenzene, bromobenzene, iodobenzene, etc. Of all these example halogenated hydrocarbons (7), the most preferred are ethyl chloride, ethyl bromide, ethyl iodide, isopropyl chloride, isopropyl bromide, isopropyl iodide, allyl chloride, allyl bromide, and allyl iodide. More than one kind of halogenated hydrocarbon (7) can be used as occasion demands.

A ratio of halogenated hydrocarbon (7) to aryl fluoride (6) is not especially limited. However, the ratio is preferably 0.5 or greater in equivalent. The ratio is more preferably in a range between 0.5 and 3.0 in equivalent, and most preferably in a range 0.8 and 1.5 in equivalent. When the ratio of halogenated hydrocarbon (7) is less than 0.5 in equivalent, there remains too much unreacted aryl fluoride (6) to produce the fluoroaryl magnesium derivative (8) effectively.

Magnesium in a shape with a large surface area, such as, powders, grains, and thin pieces (ribbons), is preferable to further promote the reaction. A ratio of magnesium to aryl fluoride (6) is not especially limited. However, the ratio is preferably 0.5 or greater in equivalent. The ratio is more preferably in a range between 0.5 and 3.0 in equivalent, and most preferably in a range between 0.8 and 1.5 in equivalent. When the ratio of magnesium is less than 0.5 in equivalent, there remains too much unreacted aryl fluoride (6) to produce the fluoroaryl magnesium derivative (8) effectively.

An order of mixing aryl fluoride (6), halide hydrocarbon (7), and magnesium with the solvent (a) is not especially limited. Examples of the mixing order are:

① aryl fluoride (6), halogenated hydrocarbon (7), and magnesium are mixed with the solvent (a) substantially at the same time;

② aryl fluoride (6) and magnesium are mixed with the solvent (a) followed by halogenated hydrocarbon (7);

③ aryl fluoride (6) is mixed with the solvent (a) first, and then halogenated hydrocarbon (7) and magnesium are mixed with the resulting solvent substantially at the same time;

④ magnesium is mixed with the solvent (a) first, and then aryl fluoride (6) and halogenated hydrocarbon (7) are mixed with the resulting solvent substantially at the same time;

⑤ magnesium, aryl fluoride (6), and halogenated hydrocarbon (7) are mixed with the solvent (a) sequentially in this order; and ⑥ aryl fluoride (6) and halogenated hydrocarbon (7) are mixed with the solvent (a) followed by magnesium.

Of all these example orders, the most preferred is to mix aryl fluoride (6) and magnesium with the solvent followed by halogenated hydrocarbon (7).

A mixing method of aryl fluoride (6) and/or halogenated hydrocarbon (7) with the solvent (a) is not especially limited. However, continuous or sequential dropping is preferable, because the reaction can be controlled more easily. A dropping method is not especially limited, and aryl fluoride (6) or halogenated hydrocarbon (7) can be dropped to the solvent (a) directly, or diluted with the solvent (a) before being dropped.

A mixing temperature at which aryl fluoride (6) and/or halogenated hydrocarbon (7) are mixed with the solvent (a) is not especially limited. However, when mixing halogenated hydrocarbon (7) with the solvent (a), a preferable mixing temperature is in a range between 20° C. and a reflux temperature of the solvent inclusive. More preferably, the mixing temperature is adjusted to be in a range between −20° C. and 100° C., and most preferably, in a range between 20° C. and 70° C. When halogenated hydrocarbon (7) is mixed with the solvent (a) within the above temperature range, the reaction can be controlled more easily. Adjusting the mixing temperature below −20° C. does not attain significant effects, and therefore, is disadvantageous for industrial use compared with a case where the mixing temperature is adjusted in the above temperature range. On the other hand, when the mixing temperature exceeds the reflux temperature of the solvent, it becomes difficult to control the reaction. The mixing temperature can be readily adjusted to be in a range between −20° C. and the reflux temperature of the solvent inclusive for industrial use.

Aryl fluoride (6), halogenated hydrocarbon (7), and magnesium start to react with one another when mixed with the above non-aqueous solvent (a) and stirred. As the reaction proceeds, magnesium gradually dissolves into the solvent (a). If there is water in the reaction system while the reaction is taking place, the resulting fluoroaryl magnesium derivative (8) decomposes by reacting with water. For this reason, it is preferable that the above reaction takes place under an inert gas atmosphere, such as a nitrogen gas. Also, it is preferable to displace the air inside the reaction system, namely, a reaction vessel, by an inert gas, such as a nitrogen gas. Further, it is preferable that the solvent (a), aryl fluoride (6), and halogenated hydrocarbon (7) do not contain water, and a desiccating method of aryl fluoride (6), halogenated hydrocarbon (7), and the solvent (a) is not especially limited.

A reaction temperature is preferably adjusted to be in a range between 30° C. and the reflux temperature of the solvent inclusive. More preferably, the reaction temperature is adjusted to be in a range between 30° C. and 200° C., and most preferably, in a range between 30° C. and 70° C. Adjusting the reaction temperature below 30° C. is not preferable, because the reaction becomes too slow to produce the fluoroaryl magnesium derivative (8) effectively. On the other hand, when the reaction temperature exceeds the reflux temperature of the solvent, it becomes difficult to control the reaction.

A reaction time can be set arbitrarily to complete the reaction depending on the reaction temperature, a combination of aryl fluoride (6) and halogenated hydrocarbon (7), a used amount of them, etc. A reaction pressure is not especially limited either, and the reaction can take place under a normal (ambient), reduced, or increased pressure.

As a result of the above process, the fluoroaryl magnesium derivative (8) is produced. In other words, a solution of the fluoroaryl magnesium derivative (8) is obtained. Also, a hydrocarbon, expressed by General Formula (D):

$$R_0H \qquad (D)$$

where $R_0$ represents a hydrocarbon group, is produced as a by-product. The hydrocarbon may be removed from the fluoroaryl magnesium derivative (8) as occasion demands, and a method of which is not especially limited.

Then, the (fluoroaryl)borane compound expressed by General Formula (9) above (hereinafter, referred to as (fluoroaryl)borane compound (9)) is obtained by reacting the fluoroaryl magnesium derivative (8) obtained in the above process and boron halide (2) in situ. A mole ratio of the fluoroaryl magnesium derivative (8) and boron halide (2) is not especially limited, but the aforementioned example range is preferable.

A mixing method of the solution of the fluoroaryl magnesium derivative (8) and boron halide (2) is not especially limited. Boron halide (2) may be added to the solution at one time, or dropped to the solution continuously or sequentially. Boron halide (2) can be dropped to the solution directly, or diluted with the solvent (a) before being dropped.

The mixing temperature and reaction temperature when mixing the fluoroaryl magnesium derivative (8) and boron halide (2) are not especially limited. However, it is preferable to adjust the mixing temperature and reaction temperature to the aforementioned example ranges. A reaction time can be set arbitrarily to complete the reaction depending on the reaction temperature, a combination of the fluoroaryl magnesium derivative (8) and boron halide (2), a used amount of them, etc. A reaction pressure is not especially limited either, and the reaction can take place under a normal (ambient), reduced, or increased pressure.

As a result of the above process, a reaction solution containing the (fluoroaryl)borane compound (9) is obtained. Then, magnesium halide produced as a by-product is separated and removed from the reaction system by adding the reaction solution to the solvent (b) while distilling out diethyl ether and/or tetrahydrofuran in the reaction solution followed by filtration. Consequently, it has become possible to produce the (fluoroaryl)borane compound (9), namely, the (fluoroaryl)borane compound (9), such as tris(fluoroaryl) borane and bis(fluoroaryl)boryl halide, from which magnesium halide expressed by General Formula (B) above is separated and removed.

Then, a reaction solution containing the tetrakis (fluoroaryl)borate derivative (10) is obtained by reacting the (fluoroaryl)borane compound (9), from which magnesium halide is separated and removed, and the fluoroaryl magnesium derivative (4). When the (fluoroaryl)borane compound (9) is bis(fluoroaryl)boryl halide, magnesium halide, which is produced as a by-product together with the tetrakis (fluoroaryl)borate derivative (10) and expressed by General Formula (C) above, dissolves into the reaction solution. Thus, to separate and remove magnesium halide, diethyl ether and/or tetrahydrofuran in the reaction solution are distilled out. On the other hand, when the (fluoroaryl)borane compound (9) is tris(fluoroaryl)borane, diethyl ether and/or tetrahydrofuran in the reaction solution are distilled out as occasion demands.

According to the above process, the tetrakis(fluoroaryl) borate derivative (10), from which magnesium halide produced as a by-product is separated and removed, can be produced in a simple manner at a low cost using aryl fluoride (6) as a starting material.

Next, a producing process of the tetrakis(fluoroaryl)borate derivative expressed by General Formula (11) above and the tetrakis(fluoroaryl)borate derivative expressed by General Formula (13) above will be explained.

The producing process of the tetrakis(fluoroaryl)borate derivative expressed by General Formula (11) above of the present invention is a process of reacting aryl fluoride (6), halogenated hydrocarbon (7), and magnesium in the ether solvent (e) or a mixed solvent of the ether solvent (e) and a hydrocarbon solvent to obtain the fluoroaryl magnesium derivative (8), and subsequently reacting the resulting fluoroaryl magnesium derivative (8) and boron halide (2) A ratio of halogenated hydrocarbon (7) to aryl fluoride (6) and a ratio of magnesium to aryl fluoride (6) are not especially limited. However, the aforementioned example ranges are preferable.

The producing process of the tetrakis(fluoroaryl)borate derivative expressed by General Formula (13) above of the present invention is a process in which, after the fluoroaryl magnesium derivative (8) is obtained, the fluoroaryl magnesium derivative (8) and tris(fluoroaryl)borane expressed by General Formula (12) above (hereinafter, referred to as the tris(fluoroaryl)borane (12)) are reacted with each other.

The ether solvent (e) is not especially limited, as long as it is a liquid compound that remains inactive to the reactions taking place in the present invention, and into which aryl fluoride (6), halogenated hydrocarbon (7), the fluoroaryl magnesium derivative (8) as an intermediate, tetrakis (fluoroaryl)borate derivative as the target product, and boron halide (2), or tris(fluroaryl)borane (12) are dissolved. Examples of the ether solvent (e) include diethyl ether, tetrahydrofuran, and the aforementioned ether solvents. One member or a mixture of two or more members selected from these examples can be used effectively. Of all these examples, the most preferred are diethyl ether and tetrahydrofuran, because the reaction takes place faster. When a mixture of two or more members selected from these examples is used, it is preferable that the mixture includes either diethyl ether or tetrahydrofuran.

An amount of the solvent (e) is not especially limited. For example, an amount in which the concentration of the resulting fluoroaryl magnesium derivative (8) is in a range between 0.1 and 80 percent by weight is preferable. The hydrocarbon solvent is not especially limited as long as it is a liquid compound that remains inactive to the reactions taking place in the present invention.

A mixing ratio of the ether solvent (e) and hydrocarbon solvent is not especially limited as long as these solvents are made into a homogeneously mixed solvent. However, the ratio is preferably in a range between 1:0 and 1:10 in volume. An amount of the mixed non-aqueous solvent is not especially limited. For example, an amount in which the concentration of the resulting fluoroaryl magnesium derivative (8) is in a range between 0.1 and 80 percent by weight is preferable.

An order of mixing aryl fluoride (6), halogenated hydrocarbon (7), and magnesium with the ether solvent (e) or a mixed solvent of the ether solvent (e) and hydrocarbon solvent (which are collectively referred to simply as the solvent (e) , hereinafter) is not especially limited. For example, the mixing orders and methods of mixing aryl fluoride (6), halogenated hydrocarbon (7), and magnesium with the solvent (a) are also applicable herein. Reaction conditions, such as mixing temperature, reaction temperature, and reaction time, when mixing aryl fluoride (6) and/or halogenated hydrocarbon (7) with the solvent (e) are not especially limited. For example, the reaction conditions, such as the mixing temperature, reaction temperature, and reaction time, used when mixing aryl fluoride (6) and/or halogenated hydrocarbon (7) with the solvent (a) are also applicable.

As a result of the above process, the fluoroaryl magnesium derivative (8) is produced. In other words, a solution of the fluoroaryl magnesium derivative (8) is obtained. Also, a hydrocarbon expressed by General Formula (D) above is produced as a by-product.

Then, the tetrakis(fluoroaryl)borate derivative expressed by General Formula (11) above (hereinafter, referred to as the tetrakis(fluoroaryl)borate derivative (11)) is obtained by reacting the fluoroaryl magnesium derivative (8) obtained by the above process with boron halide (2) in situ. Also, the tetrakis(fluoroaryl)borate derivative expressed by General Formula (13) above (hereinafter, referred to as the tetrakis (fluoroaryl)borate derivative (13)) is obtained by reacting the fluoroaryl magnesium derivative (8) and tris(fluoroaryl) borane (12) in situ.

A ratio of boron halide (2) to the fluoroaryl magnesium derivative (8) is not especially limited. However, a ratio near the theoretical ratio, that is, 0.25 in equivalent, is preferable. When the ratio is far larger or smaller than 0.25 in equivalent, the tetrakis(fluoroaryl)borate derivative (11) can not be produced effectively.

A mixing method of the solution of the fluoroaryl magnesium derivative (8) and boron halide (2) is not especially limited. Boron halide (2) may be added to the solution at one time, or dropped to the solution continuously or sequentially. Boron halide (2) may be mixed directly or diluted with the solvent (e) before being mixed.

A mixing temperature when mixing the solution of the fluoroaryl magnesium derivative (8) and boron halide (2) is not especially limited. However, the mixing temperature is preferably adjusted to be in a range between $-20°$ C. and the reflux temperature of the solvent inclusive, more preferably in a range between $-20°$ C. and $100°$ C., and most preferably in a range $20°$ C. and $70°$ C. Because when the above two substances are mixed within the above temperature range, the reaction can be controlled more easily, thereby making it possible to produce the tetrakis(fluoroaryl)borate derivative (11) more effectively in a simpler manner. Adjusting the mixing temperature below $-20°$ C. does not attain significant effects, and therefore, is disadvantageous for industrial use compared with a case where the mixing temperature is adjusted in the above temperature range. On the other hand, when the mixing temperature exceeds the reflux temperature of the solvent, it becomes difficult to control the reaction.

When the solution of the fluoroaryl magnesium derivative (8) and boron halide (2) are mixed and stirred, the fluoroaryl magnesium derivative (8) and boron halide (2) start to react with each other in the resulting solution. If there is water in the reaction system while the reaction is taking place, the fluoroaryl magnesium derivative (8) decomposes by reacting with water. For this reason, it is preferable that the above reaction takes place under an inert gas atmosphere, such as a nitrogen gas. Also, it is preferable to displace the air inside the reaction system, namely, a reaction vessel, by an inert gas, such as a nitrogen gas, when mixing the two substances. Further, it is preferable that boron halide (2) does not contain water.

A reaction temperature is preferably adjusted to be in a range between $30°$ C. and the reflux temperature of the solvent inclusive. More preferably, the reaction temperature is adjusted to be in a range between $50°$ C. and the reflux temperature of the solvent inclusive, and most preferably, in a range between $60°$ C. and reflux temperature of the solvent inclusive. Because when the reaction takes place within the above temperature range, the reaction can be controlled more easily, thereby making it possible to produce the tetrakis(fluoroaryl)borate derivative (11) more effectively in a simpler manner. Adjusting the reaction temperature below $30°$ C. is not preferable, because the reaction becomes too slow to produce the tetrakis(fluoroaryl)borate derivative (11) effectively. On the other hand, when the reaction temperature exceeds the reflux temperature of the solvent, it becomes difficult to control the reaction.

A reaction time can be set arbitrarily to complete the reaction depending on the reaction temperature, a combination of fluoroaryl magnesium derivative (8) and boron halide (2), a used amount of them, etc. A reaction pressure is not especially limited either, and the reaction can take place under a normal (ambient), reduced, or increased pressure.

As a result of the above process, the tetrakis(fluoroaryl) borate derivative (11) is produced. Also, magnesium halide expressed by General Formula (B) above is produced as a by-product. Magnesium halide can be removed from the tetrakis(fluoroaryl)borate derivative (11) as occasion demands, and a method of which is not especially limited.

Tris(fluoroaryl)borane (12) is a compound, in which each of substituent groups denoted as $R_{11}$–$R_{25}$ is a hydrogen atom, a fluorine atom, a hydrocarbon group, or an alkoxy group while at least one of $R_{11}$–$R_{25}$ is a fluorine atom. Examples of the hydrocarbon group and alkoxy group are the aforementioned examples of the hydrocarbon group and alkoxy group serving as the substituent groups denoted as $R_2$–$R_4$ in aryl fluoride (6). The tris(fluoroaryl)borane (12) is preferably a compound, in which at least one of the substituent groups denoted as $R_{11}$–$R_{15}$, at least one of the substituent groups denoted as $R_{16}$–$R_{20}$, and at least one of the substituent groups denoted as $R_{21}$–$R_{25}$ are fluorine atoms, respectively, in other words, a compound whose three aryl groups bonded to a boron atom are fluoro-substituted.

Examples of tris(fluoroaryl)borane (12) are: tris(pentafluorophenyl)borane, tris(2,3,4,6-tetrafluorophenyl)borane, tris(2,3,5,6-tetrafluorophenyl)borane, tris(2,3,5-trifluorophenyl)borane, tris(2,4,6-trifluorophenyl)borane, tris(1,3-difluorophenyl)borane, tris(2,3,5,6-tetrafluoro-4-methylphenyl)borane, tris(2,3,4,6-tetrafluoro-5-methylphenyl)borane, tris(2,4,5-trifluoro-6-methylphenyl)borane, tris(2,3,6-trifluoro-4-methylphenyl)borane, tris(2,4,6-trifluoro-3-methylphenyl)borane, tris(2,6-difluoro-3-methylphenyl)borane, tris(2,4-difluoro-5-methylphenyl)borane, tris(3,5-difluoro-2-methylphenyl)borane, tris(4-methoxy-2,3,5,6-tetrafluorophenyl)borane, tris(3-methoxy-2,4,5,6-tetrafluorophenyl)borane, tris(2-methoxy-3,5,6-trifluorophenyl)borane, tris(3-methoxy-2,5,6-trifluorophenyl)borane, tris(3-methoxy-2,4,6-trifluorophenyl)borane, tris(2-methoxy-3,5-difluorophenyl)borane, tris(3-methoxy-2,6-difluorophenyl)borane, tris(3-methoxy-4,6-difluorophenyl)borane, tris(2-methoxy-4,6-difluorophenyl)borane, tris(4-methoxy-2,6-difluorophenyl)borane, etc. Of all these example compounds, the most preferred is tris(pentafluorophenyl)borane. More than one kind of tris(fluoroaryl)borane (12) can be used as occasion demands.

A ratio of tris(fluoroaryl)borane (12) to the fluoroaryl magnesium derivative (8) is not especially limited. However, a ratio near the theoretical ratio, that is, 1.0 in equivalent, is preferable. When the ratio is far larger or smaller than 1.0 in equivalent, the tetrakis(fluoroaryl)borate derivative (13) can not be produced effectively.

A mixing method of the solution of the fluoroaryl magnesium derivative (8) and tris(fluoroaryl)borane (12) is not especially limited. Tris(fluoroaryl)borane (12) may be added to the solution at one time, or dropped to the solution continuously or sequentially. Tris(fluoroaryl)borane (12) may be mixed directly or diluted with the solvent (e) before being mixed.

A mixing temperature when mixing the solution of the fluoroaryl magnesium derivative (8) and tris(fluoroaryl)borane (12) is not especially limited. However, the mixing temperature is preferably adjusted to be in a range between −20° C. and the reflux temperature of the solvent inclusive, more preferably in a range between −20° C. and 100° C., and most preferably in a range 20° C. and 70° C. Because when the above two substances are mixed within the above temperature range, the reaction can be controlled more easily, thereby making it possible to produce the tetrakis(fluoroaryl)borate derivative (13) more effectively in a simpler manner. Adjusting the mixing temperature below −20° C. does not attain significant effects, and therefore, is disadvantageous for industrial use compared with a case where the mixing temperature is adjusted in the above temperature range. On the other hand, when the mixing temperature exceeds the reflux temperature of the solvent, it becomes difficult to control the reaction.

When the solution of the fluoroaryl magnesium derivative (8) and tris(fluoroaryl)borane (12) are mixed and stirred, the fluoroaryl magnesium derivative (8) and tris(fluoroaryl)borane (12) start to react with each other in the resulting solution. It is preferable that the above reaction takes place under an inert gas atmosphere, such as a nitrogen gas. Also, it is preferable to displace the air inside the reaction system, namely, a reaction vessel, by an inert gas, such as a nitrogen gas, when the two substances are mixed. Further, it is preferable that tris(fluoroaryl)borane (12) does not contain water, and a desiccating method of tris(fluoroaryl)borane (12) is not especially limited.

A reaction temperature is preferably adjusted to be in a range between 30° C. and the reflux temperature of the solvent inclusive. More preferably, the reaction temperature is adjusted to be in a range between 50° C. and the reflux temperature of the solvent inclusive, and most preferably, in a range between 60° C. and reflux temperature of the solvent inclusive. When the reaction takes place within the above temperature range, the reaction can be controlled more easily, thereby making it possible to produce the tetrakis(fluoroaryl)borate derivative (13) more effectively in a simpler manner. Adjusting the reaction temperature below 30° C. is not preferable, because the reaction becomes too slow to produce the tetrakis(fluoroaryl)borate derivative (13) effectively. On the other hand, when the reaction temperature exceeds the reflux temperature of the solvent, it becomes difficult to control the reaction.

A reaction time can be set arbitrarily to complete the reaction depending on the reaction temperature, a combination of the fluoroaryl magnesium derivative (8) and tris(fluoroaryl)borane (12), a used amount of them, etc. A reaction pressure is not especially limited either, and the reaction can take place under a normal (ambient), reduced, or increased pressure.

As a result of the above process, the tetrakis(fluoroaryl)borate derivative (13) is produced. Also, according to the above process, the tetrakis(fluoroaryl)borate derivative (13), in which at least one of four fluoroaryl groups bonded to a boron atom has a different structure from the others.

As has been explained, the producing process of the tetrakis(fluoroaryl)borate derivative (11) of the present invention is a process of reacting aryl fluoride (6), halogenated hydrocarbon (7), and magnesium in the solvent (e) to obtain the fluoroaryl magnesium derivative (8), and subsequently reacting the resulting fluoroaryl magnesium derivative (8) and boron halide (2).

Also, as has been explained, the producing process of the tetrakis(fluoroaryl)borate derivative (13) of the present invention is a process, in which, after the fluoroaryl magnesium derivative (8) is obtained, the fluoroaryl magnesium derivative (8) is reacted with tris(fluoroaryl)borane (12).

According to these processes, the reaction takes place virtually in a single step. Also, according to the above processes, the tetrakis(fluoroaryl)borate derivatives (11) and (13) can be obtained at high yield and selectivity. Consequently, the tetrakis(fluoroaryl)borate derivatives (11) and (13) can be produced effectively in a simple manner at a low cost. The tetrakis(fluoroaryl)borate derivatives (11) and (13) are useful, for example, as a cocatalyst for metallocene catalysts (polymerization catalyst) used in a cation complex polymerization reaction. Note that the tetrakis (fluoroaryl)borate derivatives (11) and (13) are relatively stable compounds, and can be isolated from the reaction system in the form of crystals or solution as occasion demands, and an isolating method is not especially limited.

In the following, the present invention will be explained in detail by way of examples. However, the present invention is not limited to the description below.

EXAMPLE 1

Air inside a reaction vessel equipped with a thermometer, a dropping funnel, a stirrer, a nitrogen gas conduit, and a reflux condenser is replaced with a nitrogen gas in a satisfactory manner. Then, 2.874 g (0.0203 mole) of boron trifluoride diethyl etherate serving as boron halide (2) and 40 ml of diethyl ether serving as the solvent (a) are charged to the reaction vessel. Also, 30 ml of a diethyl ether solution (the solution of the magnesium derivative (1)) containing 0.0624 mole of pentafluorophenyl magnesium bromide serving as the fluoroaryl magnesium derivative (1) is placed in the dropping funnel. A concentration of pentafluorophenyl magnesium bromide in the diethyl ether solution is 2.08 mole/L. A mole ratio of pentafluorophenyl magnesium bromide to the boron trifluoride diethyl etherate is 3.1.

Next, the diethyl ether solution is dropped to the above contents (the solution of boron halide (2)) over 20 minutes with stirring under a nitrogen gas atmosphere. The temperature of the contents at the beginning of the dropping was 31° C. (mixing temperature) and has risen up to 36° C. during the dropping. After the completion of the dropping, the reaction solution is subject to reaction (maturing) for three hours at 34° C. (reaction temperature) with stirring. Consequently, a diethyl ether solution of crude tris (pentafluorophenyl)borane as the (fluoroaryl)borane compound (3) is obtained.

Then, 300 ml of toluene serving as the solvent (b) is charged to a still equipped with a thermometer, a dropping funnel, a stirrer, and a Liebig condenser. The edge of the outlet of the Liebig condenser is open and a receiver is provided at a predetermined position. Also, the diethyl ether solution of crude tris(pentafluorophenyl)borane is charged to the dropping funnel.

Then, toluene is heated to 80° C. with stirring, after which the diethyl ether solution within the dropping funnel is dropped to toluene over 1 hour while keeping toluene at 80° C. The distilling-out of diethyl ether under a normal pressure is started concurrently with the dropping. After the completion of the dropping, the contents (mixed substance) in the still are heated to 110° C., so that diethyl ether is distilled out almost completely.

After the completion of the distilling-out of diethyl ether, the contents are cooled to room temperature. Subsequently, the contents are filtered under a nitrogen gas atmosphere to remove magnesium fluoride bromide produced as a by-product from tris(pentafluorophenyl)borane. Consequently, tris(fluorophenyl)borane, from which magnesium fluoride bromide is removed, is obtained in the form of a toluene solution (filtrate).

The yield of tris(pentafluorophenyl)borane is found by measuring $^{19}$F-NMR. More specifically, $^{19}$F-NMR is measured under predetermined conditions using p-fluorotoluene as an internal standard reagent. Then, a peak integral of a fluorine atom of p-fluorotoluene, and a peak integral of fluorine atoms at the ortho-position of a pentafluorophenyl group in tris(pentafluorophenyl)borane are computed from the resulting $^{19}$F-NMR chart first, and then an amount of tris(pentafluorophenyl)borane is computed using the above two peak integrals. Consequently, a reaction yield of tris (pentafluorophenyl)borane based on pentafluorophenyl magnesium bromide thus found is 81.8 percent by mole at a purity of 93.2%.

EXAMPLE 2

Air inside a reaction vessel of the same kind as the one used in Example 1 is displaced by a nitrogen gas in a satisfactory manner. Then, 5.238 g (0.0369 mole) of boron trifluoride diethyl etherate and 50 ml of diethyl ether are charged to the reaction vessel. Also, 50 ml of diethyl ether solution containing 0.1151 mole of pentafluorophenyl magnesium bromide is charged to the dropping funnel. A concentration of pentafluorophenyl magnesium bromide in the diethyl ether solution is 2.30 mole/L. A mole ratio of pentafluorophenyl magnesium bromide to the boron trifluoride diethyl etherate is 3.1. Next, the diethyl ether solution is dropped to the above contents over 30 minutes with stirring under a nitrogen gas atmosphere. The temperature of the contents at the beginning of the dropping was 31° C. and has risen to 37° C. during the dropping. After the completion of the dropping, the reaction solution is subject to reaction (maturing) for 3 hours at 35° C. with stirring. Consequently, the diethyl crude ether solution of tris(pentafluorophenyl) borane is obtained.

Then, 300 ml of cyclohexane serving as the solvent (b) is charged to a still of the same kind as the one used in Example 1. Also, the diethyl ether solution of crude tris (pentafluorophenyl)borane is charged to the dropping funnel. Then, the cyclohexane is heated to 70° C. with stirring, after which the diethyl ether solution within the dropping funnel is dropped to the cyclohexane over 1 hour while keeping the cyclohexane at 70° C. The distilling-out of diethyl ether under a normal pressure is started concurrently with the dropping. After the completion of the dropping, the contents in the still are heated to 80° C., so that diethyl ether is distilled out almost completely.

After the completion of the distilling-out of diethyl ether, the contents are cooled to room temperature. Subsequently, tris(pentafluorophenyl)borane, from which magnesium fluoride bromide produced as a by-product is removed, is obtained in the form of a cyclohexane solution in the same manner as Example 1. A reaction yield of tris (pentafluorophenyl)borane found in the same manner as Example 1 is 88.3 percent by mole at a purity of 94.7%.

EXAMPLE 3

Air inside a reaction vessel of the same kind as the one used in Example 1 is displaced by a nitrogen gas in a satisfactory manner. Then, 7.432 g (0.0520 mole) of boron trifluoride diethyl etherate and 70 ml of diethyl ether are charged to the reaction vessel. Also, 70 ml of diethyl ether solution containing 0.1129 mole of pentafluorophenyl magnesium bromide is charged to the dropping funnel. A concentration of pentafluorophenyl magnesium bromide in the diethyl ether solution is 2.26 mole/L. A mole ratio of pentafluorophenyl magnesium bromide to the boron trifluoride diethyl etherate is 2.2. Next, the diethyl ether solution is dropped to the above contents over 30 minutes with stirring under a nitrogen gas atmosphere. The temperature of the contents at the beginning of the dropping was 29° C. and has risen to 36° C. during the dropping. After the completion of the dropping, the reaction solution is subject to reaction (maturing) for 3 hours at 35° C. with stirring. Consequently, a diethyl ether solution of crude tris(pentafluorophenyl) borane is obtained.

Then, 300 ml of xylene serving as the solvent (b) is charged to a still of the same kind as the one used in Example 1. Also, the diethyl ether solution of crude tris (pentafluorophenyl)borane is charged to the dropping funnel. Then, the xylene is heated to 80° C. with stirring, after which the diethyl ether solution within the dropping funnel is dropped to the xylene over 1 hour while keeping the xylene at 80° C. The distilling-out of diethyl ether under a normal pressure is started concurrently with the dropping. After the completion of the dropping, the contents in the still are heated to 135° C., so that diethyl ether is distilled out almost completely.

After the completion of the distilling-out of diethyl ether, the contents are cooled to room temperature. Subsequently, tris(pentafluorophenyl)borane, from which magnesium fluoride bromide produced as a by-product is removed, is obtained in the form of a xylene solution of in the same manner as Example 1. A reaction yield of tris (pentafluorophenyl)borane found in the same manner as Example 1 is 92.0 percent by mole at a purity of 91.9%.

EXAMPLE 4

A diethyl ether solution of crude tris(pentafluorophenyl) borane is obtained in the same manner as Example 3. Then, 300 ml of n-octane serving as the solvent (b) is charged to a still of the same kind as the one used in Example 1. Also, the diethyl ether solution of crude tris(pentafluorophenyl) borane is charged to the dropping funnel. Then, the n-octane is heated to 80° C. with stirring, after which the diethyl ether solution within the dropping funnel is dropped octane over 1 hour while keeping the n-octane at 80° C. The distilling-out of diethyl ether under a normal pressure is started concurrently with the dropping. After the completion of the dropping, the contents in the still are heated to 110° C., so that diethyl ether is distilled out almost completely.

After the completion of the distilling-out of diethyl ether, the contents are cooled to room temperature. Subsequently, tris(pentafluorophenyl)borane, from which magnesium fluoride bromide produced as a by-product is removed, is obtained in the form of an n-octane solution in the same manner as Example 1. A reaction yield of tris (pentafluorophenyl)borane found in the same manner as Example 1 is 92.0 percent by mole at a purity of 92.5%.

EXAMPLE 5

Air inside a reaction vessel of the same kind as the one used in Example 1 is displaced by a nitrogen gas in a satisfactory manner. Then, 8.040 g (0.0569 mole) of boron trifluoride diethyl etherate and 60 ml of diethyl ether are charged to the reaction vessel. Also, 110 ml of diethyl ether solution containing 0.1707 mole of pentafluorophenyl magnesium bromide is charged to the dropping funnel. A concentration of pentafluorophenyl magnesium bromide in the diethyl ether solution is 1.54 mole/L. A mole ratio of pentafluorophenyl magnesium bromide to the boron trifluoride diethyl etherate is 3.0. Next, the diethyl ether solution is dropped to the above contents over 1 hour with stirring under a nitrogen gas atmosphere. The temperature of the contents at the beginning of the dropping was 30° C. and has risen up to 32° C. during the dropping. After the completion of the dropping, the reaction solution is subject to reaction (maturing) for 3 hours at 35° C. with stirring. Consequently, a diethyl ether solution of crude tris(pentafluorophenyl) borane is obtained.

Then, 250 ml of dibutyl ether serving as the solvent (b) is charged to a still of the same kind as the one used in Example 1. Also, the diethyl ether solution of crude tris (pentafluorophenyl)borane is charged to the dropping funnel. Then, the dibutyl ether is heated to 95° C. with stirring, after which the diethyl ether solution within the dropping funnel is dropped to the dibutyl ether over 1 hour while keeping the dibutyl ether at 95° C. The distilling-out of diethyl ether under a normal pressure is started concurrently with the dropping. After the completion of the dropping, the contents in the still is heated to 110° C., so that diethyl ether is distilled out almost completely.

After the completion of the distilling-out of diethyl ether, the content are cooled to room temperature. Subsequently, tris(pentafluorophenyl)borane, from which magnesium fluoride bromide produced as a by-product is removed, is obtained in the form of a dibutyl ether solution in the same manner as Example 1. A reaction yield of tris (pentafluorophenyl)borane found in the same manner as Example 1 is 86.8 percent by mole at a purity of 89.8%.

EXAMPLE 6

Air inside a reaction vessel of the same kind as the one used in Example 1 is displaced by a nitrogen gas in a satisfactory manner. Then, 2.695 g (0.0191 mole) of boron trifluoride diethyl etherate, 20 ml of diethyl ether and 20 ml of toluene both serving as the solvent (a) are charged to the reaction vessel. Also, 50 ml of a mixed solution of diethyl ether and toluene containing 0.0600 mole of pentafluorophenyl magnesium bromide is charged to the dropping funnel. A mixing ratio of diethyl ether to toluene in the resulting mixed solution is 2:1. Also, a concentration of pentafluorophenyl magnesium bromide in the mixed solution is 1.20 mole/L. Further, a mole ratio of pentafluorophenyl magnesium bromide to the boron trifluoride diethyl etherate is 3.1.

Next, the mixed solution is dropped to the above contents over 1 hour with stirring under a nitrogen gas atmosphere. The temperature of the contents at the beginning of the dropping was 28° C. and has risen up to 35° C. during the dropping. After the completion of the dropping, the reaction solution is subject to reaction (maturing) for 1 hour at 40° C. with stirring. Consequently, a mixed solution of diethyl ether and toluene of crude tris(pentafluorophenyl)borane is obtained.

Then, 100 ml of toluene serving as the solvent (b) is charged to a still of the same kind as the one used in Example 1. Also, the mixed solution of diethyl ether and toluene of crude tris(pentafluorophenyl)borane is charged to the dropping funnel. Then, the toluene is heated to 100° C. with stirring, after which the mixed solution within the dropping funnel is dropped to the toluene over 1 hour while keeping the toluene at 100° C. The distilling-out of diethyl ether under a normal pressure is started concurrently with the dropping. After the completion of the dropping, the contents in the still is heated to 110° C., so that diethyl ether is distilled out almost completely.

After the completion of the distilling-out of diethyl ether, the contents are cooled to room temperature. Subsequently, tris(pentafluorophenyl)borane, from which magnesium fluoride bromide produced as a by-product is removed, is obtained in the form of a toluene solution in the same manner as Example 1. A reaction yield of tris (pentafluorophenyl)borane found in the same manner as Example 1 is 82.7 percent by mole at a purity of 91.0%.

EXAMPLE 7

Air inside a reaction vessel of the same kind as the one used in Example 1 is displaced by a nitrogen gas in a satisfactory manner. Then, 16.95 g (0.120 mole) of boron trifluoride diethyl etherate and 150 ml of diethyl ether are charged to the reaction vessel. Also, 300 ml of diethyl ether solution containing 0.360 mole of pentafluorophenyl magnesium bromide is charged to the dropping funnel. A concentration of pentafluorophenyl magnesium bromide in the diethyl ether solution is 1.20 mole/L. Further, a mole ratio of pentafluorophenyl magnesium bromide to the boron trifluoride diethyl etherate is 3.0. Next, the diethyl ether solution is dropped to the above contents over 90 minutes with stirring under a nitrogen gas atmosphere. The temperature of the contents at the beginning of the dropping was 28° C. and has risen to 34° C. during the dropping. After the completion of the dropping, the reaction solution is subject to reaction (maturing) for 3 hours at 35° C. with stirring. Consequently, a diethyl ether solution of crude tris(pentafluorophenyl) borane is obtained.

Then, 500 ml of toluene is charged to a still of the same kind as the one used in Example 1. Also, the diethyl ether solution of crude tris(pentafluorophenyl)borane is charged to the dropping funnel. Then, the toluene is heated to 35° C. with stirring, after which the diethyl ether solution within the dropping funnel is dropped to the toluene over 90 minutes while keeping the toluene at 35° C. When the completion of the dropping, the temperature of the so contents (mixed substance) in the still is raised gradually up to 110° C., while the distilling-out of diethyl ether under a normal pressure is started, so that diethyl ether is distilled out almost completely.

After the completion of the distilling-out of diethyl ether, the contents are cooled to room temperature. Subsequently, the contents are filtered under a nitrogen gas atmosphere, so that tris(pentafluorophenyl)borane is separated from magnesium fluoride bromide produced as a by-product together with the tris(pentafluorophenyl)borane. Although a considerable amount of magnesium fluoride bromide adheres to the inner wall of the still, no inconvenience is caused during the filtration. Consequently, tris(pentafluorophenyl)borane, from which magnesium fluoride bromide produced as a by-product is removed, is obtained in the form of a toluene solution in the same manner as Example 1. A reaction yield of tris(pentafluorophenyl)borane found in the same manner as Example 1 is 75.0 percent by mole at a purity of 85.5%.

EXAMPLE 8

A tetrakis(pentafluorophenyl)borate derivative as the tetrakis(fluoroaryl)borate derivative (5) is produced using the toluene solution of tris(pentafluorophenyl)borane obtained in Example 1.

Air inside a reaction vessel equipped with a thermometer, a dropping funnel, a stirrer, a nitrogen gas conduit, and a Liebig condenser is displaced by a nitrogen gas in a satisfactory manner. Then, 35 ml of a diethyl ether solution (the solution of the magnesium derivative (4)) containing 0.059 mole of pentafluorophenyl magnesium bromide serving as the fluoroaryl magnesium derivative (4) is charged to the reaction vessel. A concentration of pentafluorophenyl magnesium bromide in the diethyl ether solution is 1.67 mole/L. Also, 116.0 g of the toluene solution of tris (pentafluorophenyl)borane obtained in Example 1 is charged to the dropping funnel. A concentration of tris (pentafluorophenyl)borane in the toluene solution is 25.0 percent by weight, and 0.057 mole of tris (pentafluorophenyl)borane is contained in 116.0 g of the toluene solution.

Next, the toluene solution is dropped to the diethyl ether solution over 30 minutes at room temperature (mixing temperature) with stirring under a nitrogen gas atmosphere. After the completion of the dropping, the contents in the reaction vessel are raised to 110° C. (reaction temperature) to let the contents undergo reaction (maturing) while diethyl ether is distilled out under a normal pressure.

After the completion of the distilling-out of diethyl ether, the contents are cooled to room temperature. Then, crystals of tetrakis(pentafluorophenyl)borate magnesium bromide salt precipitates and deposits as tetrakis(fluoroaryl)borate derivative (5). Subsequently, the contents are filtered to isolate the crystals. As a result, 27.8 g of tetrakis (pentafluorophenyl)borate magnesium bromide salt is obtained at a yield of 62.7 percent by mole.

Further, the filtrate is heated under a reducing pressure to distill out toluene, and an amount of tetrakis (pentafluorophenyl)borate magnesium bromide salt contained in the residue is measured in the same manner as Example 1. Then, it turned out that tetrakis (pentafluorophenyl)borate magnesium bromide salt is contained in the residue in an amount corresponding to 2.0 percent by mole in yield. Thus, an overall yield of tetrakis (pentafluorophenyl)borate magnesium bromide salt is 64.7 percent by mole.

EXAMPLE 9

A tetrakis(pentafluorophenyl)borate derivative is produced using the cyclohexane solution of tris (pentafluorophenyl)borane obtained in Example 2.

Air inside a reaction vessel of the same kind as the one used in Example 8 is displaced by a nitrogen gas in a satisfactory manner. Then, 20 ml of a diethyl ether solution containing 0.008 mole of pentafluorophenyl magnesium bromide is charged to the reaction vessel. A concentration of pentafluorophenyl magnesium bromide in the diethyl ether solution is 0.374 mole/L. Also, 118.3 g of the cyclohexane solution of tris(pentafluorophenyl)borane obtained in Example 2 is charged to the dropping funnel. A concentration of tris(pentafluorophenyl)borane in the cyclohexane solution is 3.24 percent by weight, and 0.007 mole of tris(pentafluorophenyl)borane is contained in 118.3 g of the cyclohexane solution.

Next, the cyclohexane solution is dropped to the diethyl ether solution over 30 minutes at room temperature with stirring under a nitrogen gas atmosphere. After the completion of the dropping, the contents in the reaction vessel are heated to 71° C. to let the contents undergo reaction (maturing) while diethyl ether is distilled out under a normal pressure.

After the completion of the distilling-out of diethyl ether, the contents are cooled to room temperature. Then, the contents separate into two layers. To be more specific, the contents seperate to an upper layer made of cyclohexane and a lower layer made of a liquid of tetrakis(pentafluorophenyl) borate magnesium bromide salt. Then, the above two layers are separated from each other in the form of liquid. Consequently, a liquid of tetrakis(pentafluorophenyl)borate magnesium bromide salt is obtained. A reaction yield of tetrakis(pentafluorophenyl)borate magnesium bromide salt is measured in the same manner as Example 1. Then, a reaction yield of tetrakis(pentafluorophenyl)borate magnesium bromide salt based on pentafluorophenyl magnesium bromide thus found is 81.2 percent by mole.

EXAMPLE 10

A tetrakis(pentafluorophenyl)borate derivative is produced using the xylene solution of tris(pentafluorophenyl) borane obtained in Example 3.

Air inside a reaction vessel of the same kind as the one used in Example 8 is displaced by a nitrogen gas in a satisfactory manner. Then, 20 ml of a diethyl ether solution containing 0.024 mole of pentafluorophenyl magnesium bromide is charged to the reaction vessel. A concentration of pentafluorophenyl magnesium bromide in the diethyl ether solution is 1.22 mole/L. Also, 92.7 g of the xylene solution of tris(pentafluorophenyl)borane obtained in Example 3 is charged to the dropping funnel. A concentration of tris (pentafluorophenyl)borane in the xylene solution is 11.84 percent by weight, and 0.021 mole of tris (pentafluorophenyl)borane is contained in 92.7 g of the xylene solution.

Next, the xylene solution is dropped to the diethyl ether solution over 30 minutes at room temperature with stirring under a nitrogen gas atmosphere. After the completion of the dropping, the contents in the reaction vessel are heated to 130° C. to let the contents undergo reaction (maturing) while diethyl ether is distilled out under a normal pressure.

After the completion of the distilling-out of diethyl ether, the contents are cooled to room temperature. Then, the contents separate into two layers: an upper layer made of xylene and a lower layer made of a liquid of tetrakis (pentafluorophenyl)borate magnesium bromide salt. Then, the above two layers are separated from each other in the form of liquid. Consequently, a liquid of tetrakis (pentafluorophenyl)borate magnesium bromide salt is obtained. A reaction yield of tetrakis(pentafluorophenyl) borate magnesium bromide salt based on pentafluorophenyl magnesium bromide measured in the same manner as Example 1 is 92.5 percent by mole.

EXAMPLE 11

A tetrakis(pentafluorophenyl)borate derivative is produced using the n-octane solution of tris(pentafluorophenyl) borane obtained in Example 4.

Air inside a reaction vessel of the same kind as the one used in Example 8 is displaced by a nitrogen gas in a satisfactory manner. Then, 10 ml of a diethyl ether solution containing 0.017 mole of pentafluorophenyl magnesium bromide is charged to the reaction vessel. A concentration of pentafluorophenyl magnesium bromide in the diethyl ether solution is 1.68 mole/L. Also, 85.4 g of the n-octane solution of tris(pentafluorophenyl)borane obtained in Example 4 is charged to the dropping funnel. A concentration of tris (pentafluorophenyl)borane in the n-octane solution is 8.89 percent by weight, and 0.015 mole of tris (pentafluorophenyl)borane is contained in 85.4 g of the n-octane solution.

Next, the n-octane solution is dropped to the diethyl ether solution over 30 minutes at room temperature with stirring under a nitrogen gas atmosphere. After the completion of the dropping, the contents in the reaction vessel are heated to 110° C. to let the contents undergo reaction (maturing) while diethyl ether is distilled out under a normal pressure.

After the completion of the distilling-out of diethyl ether, the contents are cooled to room temperature. Then, the contents separate into two layers: an upper layer made of n-octane and a lower layer made of a liquid of tetrakis (pentafluorophenyl)borate magnesium bromide salt. Then, the above two layers are separated from each other in the form of liquid. Consequently, a liquid of tetrakis (pentafluorophenyl)borate magnesium bromide salt is obtained. A reaction yield of tetrakis(pentafluorophenyl) borate magnesium bromide salt based on pentafluorophenyl magnesium bromide found in the same manner as Example 1 is 77.1 percent by mole.

EXAMPLE 12

A tetrakis(pentafluorophenyl)borate derivative is produced using the dibutyl ether solution of tris (pentafluorophenyl)borane obtained in Example 5.

Air inside a reaction vessel of the same kind as the one used in Example 8 is displaced by a nitrogen gas in a satisfactory manner. Then, 37 ml of a diethyl ether solution containing 0.050 mole of pentafluorophenyl magnesium bromide is charged to the reaction vessel. A concentration of pentafluorophenyl magnesium bromide in the diethyl ether solution is 1.34 mole/L. Also, 139.0 g of the dibutyl ether solution of tris(pentafluorophenyl)borane obtained in Example 5 is charged to the dropping funnel. A concentration of tris(pentafluorophenyl)borane in the dibutyl ether solution is 18.2 percent by weight, and 0.049 mole of tris(pentafluorophenyl)borane is contained in 139.0 g of the dibutyl ether solution.

Next, the dibutyl ether solution is dropped to the diethyl ether solution over 30 minutes at room temperature with stirring under a nitrogen gas atmosphere. After the completion of the dropping, the contents in the reaction vessel are raised to 137° C. to let the contents undergo reaction (maturing) while diethyl ether is distilled out under a normal pressure.

After the completion of the distilling-out of diethyl ether, the contents are cooled to room temperature. Then, the contents separate into two layers: an upper layer made of dibutyl ether and a lower layer made of a liquid of the tetrakis(pentafluorophenyl)borate dibutyl ether complex. Then, the above two layers are separated from each other in the form of liquid. Consequently, a liquid of the tetrakis (pentafluorophenyl)borate dibutyl ether complex is obtained. A reaction yield of the tetrakis(pentafluorophenyl) borate dibutyl ether complex based on pentafluorophenyl magnesium bromide found in the same manner as Example 1 is 92.8 percent by mole.

EXAMPLE 13

Air inside a reaction vessel equipped with a thermometer, a dropping funnel, a stirrer, a nitrogen gas conduit, and a reflux condenser is displaced by a nitrogen gas in a satisfactory manner. Then, 1.027 g (0.042 mole) of magnesium, 6.810 g(0.041 mole) of pentafluorobenzene serving as aryl fluoride (6), and 20 ml of diethyl ether serving as the solvent (e) (ether solvent (e)) are charged to the reaction vessel. Also, 4.945 g (0.040 mole) of isopropyl bromide serving as halogenated hydrocarbon (7) is charged to the dropping funnel.

Then, isopropyl bromide is dropped to the above contents with the stirring under a nitrogen gas flow. After the completion of the dropping, the resulting reaction solution is subject to reaction (maturing) for 3 hours at 51.0° C. (reaction temperature) with stirring. Consequently, pentafluorophenyl magnesium bromide as the fluoroaryl magnesium derivative (8) is obtained in the form of a diethyl ether solution.

A reaction yield of pentafluorophenyl magnesium bromide is found by measuring $^{19}$F-NMR. More specifically, a part of the reaction solution is put aside when the reaction ends, and a measuring sample is prepared by mixing the same with deuterobenzene under a nitrogen gas atmosphere. Here, $^{19}$F-NMR is measured under predetermined conditions. Then, a peak integral of two fluorine atoms at the meta-position of pentafluorobenzene, and a peak integral of two fluorine atoms at the meta-position of pentafluorophenyl group in pentafluorophenyl magnesium bromide are computed from the resulting $^{19}$F-NMR chart first, and then an amount of pentafluorophenyl magnesium bromide is computed using the above two peak integrals. Then, a reaction yield of pentafluoromagnesium bromide thus found is 81.8 percent by mole.

Subsequently, 1.227 g (0.009 mole) of boron trifluoride diethyl etherate serving as boron halide (2) is added to the reaction vessel while holding pentafluorophenyl magnesium bromide therein under a nitrogen gas flow, and both the substances stirred and mixed. The temperature of the contents during the mixing (mixing temperature) has risen up to 66.0° C., after which the resulting reaction solution is subject to reaction for 2 hours with stirring. Consequently, a tetrakis(pentafluorophenyl)borate derivative as the tetrakis (fluoroaryl)borate derivative (11) is obtained in the form of a diethyl ether solution.

A reaction yield of the tetrakis(pentafluorophenyl)borate derivative is measured by measuring $^{19}$F-NMR using p-fluorotoluene as an internal standard reagent. Consequently, a reaction yield of the tetrakis (pentafluorophenyl)borate derivative is 81.6 percent by mole.

EXAMPLE 14

Air inside a reaction vessel of the same kind as the one used in Example 13 is displaced by a nitrogen gas in a satisfactory manner. Then, 2.040 g (0.084 mole) of magnesium, 13.577 g (0.081 mole) of pentafluorobenzene, and 20 ml of diethyl ether are charged to the reaction vessel. Also, 10.518 g (0.081 mole) of isopropyl bromide is charged to the dropping funnel. Next, isopropyl bromide is dropped to the above contents with stirring under a nitrogen gas flow. After the completion of the dropping, the resulting reaction solution is subject to reaction for 3 hours at 63.0° C. with stirring. Consequently, pentafluorophenyl magnesium bromide is obtained in the form of a diethyl ether solution. A reaction yield of pentafluorophenyl magnesium bromide found in the same manner as Example 13 is 80.3 percent by mole.

Next, 2.248 g (0.016 mole) of boron trifluoride diethyl etherate is added to the above reaction vessel while holding pentafluorophenyl magnesium bromide therein under a nitrogen gas flow, and the two substances are mixed and stirred. The temperature of the contents during the mixing (mixing temperature) has risen up to 63.0° C. Then, the reaction solution is subject to reaction for 2 hours with stirring. Consequently, a tetrakis(pentafluorophenyl)borate derivative is obtained in the form of a diethyl ether solution. A reaction yield of the tetrakis(pentafluorophenyl)borate derivative found in the same manner as Example 13 is 79.6 percent by mole.

EXAMPLE 15

Air inside a reaction vessel of the same kind as the one used in Example 13 is displaced by a nitrogen gas in a satisfactory manner. Then, 2.650 g (0.109 mole) of magnesium, 17.469 g (0.104 mole) of pentafluorobenzene, and 10 ml of diethyl ether and 10 ml of toluene both serving as the solvent (e) (mixed solvent) are charged to the reaction vessel. Also, 14.185 g (0.109 mole) of isopropyl bromide is charged to the dropping funnel. Next, isopropyl bromide is dropped to the contents with stirring under a nitrogen gas atmosphere. After the completion of the dropping, the resulting reaction solution is subject to reaction for 2.5 hours at 69.0° C. with stirring. Consequently, pentafluorophenyl magnesium bromide is obtained in the form of a mixed solution of diethyl ether and toluene. A reaction yield of pentafluorophenyl magnesium bromide found in the same manner as Example 13 is 82.4 percent by mole.

Next, 2.190 g (0.015 mole) of boron trifluoride diethyl etherate is added to the above reaction vessel while holding pentafluorophenyl magnesium bromide therein under a nitrogen gas flow, and the two substances are mixed and stirred. The temperature of the contents during the mixing (mixing temperature) has risen up to 78.0° C. Then, the resulting reaction solution is subject to reaction for 2 hours with stirring. Consequently, a tetrakis(pentafluorophenyl) borate derivative is obtained in the form of a mixed solution of diethyl ether and toluene. A reaction yield of the tetrakis (pentafluorophenyl)borate derivative found in the same manner as Example 13 is 80.4 percent by mole.

EXAMPLE 16

Air inside a reaction vessel of the same kind as the one used in Example 13 is displaced by a nitrogen gas in a satisfactory manner. Then, 2.025 g (0.083 mole) of magnesium, 13.198 g (0.079 mole) of pentafluorobenzene, and 20 ml of tetrahydrofuran (THF) serving as the solvent (e) (ether solvent (e)) are charged to the reaction vessel. Also, 10.782 g (0.083 mole) of isopropyl bromide is charged to the dropping funnel. Next, isopropyl bromide is dropped to the above contents with stirring under a nitrogen gas flow. After the completion of the dropping, the resulting reaction solution is subject to reaction for 2 hours at 57.0° C. with stirring. Consequently, pentafluorophenyl magnesium bromide is obtained in the form of a THF solution. A reaction yield of pentafluorophenyl magnesium bromide found in the same manner as Example 13 is 82.9 percent by mole.

Next, 2.005 g (0.014 mole) of a boron trifluoride THF complex serving as boron halide (2) is added to the above reaction vessel while holding pentafluorophenyl magnesium bromide therein under a nitrogen gas flow, and the two substances are stirred and mixed. The temperature of the contents during the mixing (mixing temperature) has risen up to 58.0° C. Then, the reaction solution is subject to reaction for 2 hours with stirring. Consequently, a tetrakis (pentafluorophenyl)borate derivative is obtained in the form of a THF solution. A reaction yield of the tetrakis (pentafluoropheyl)borate found in the same manner as Example 13 is 73.7 percent by mole.

EXAMPLE 17

Air inside a reaction vessel of the same kind as the one used in Example 13 is displaced by a nitrogen gas in a satisfactory manner. Then, 2.008 g (0.082 mole) of magnesium, 13.529 g (0.081 mole) of pentafluorobenzene, and 20 ml of diethyl ether are charged to the reaction vessel. Also, 10.873 g (0.084 mole) of isopropyl bromide is charged to the dropping funnel. Next, isopropyl bromide is dropped to the above contents with stirring under a nitrogen gas flow. After the completion of the dropping, the resulting reaction solution is subject to reaction for 2 hours at 57.0° C. with stirring. Consequently, pentafluorophenyl magnesium bromide is obtained in the form of a diethyl ether solution. A reaction yield of pentafluorophenyl magnesium bromide found in the same manner as Example 13 is 80.3 percent by mole.

Next, 652.9 g (0.055 mole) of a solution, which is prepared by dissolving tris(pentafluorophenyl)borane serving as tris(fluoroaryl)borane (12) into cyclohexane (hydrocarbon solvent) in such a manner that a concentration of tris(pentafluorophenyl)borane is 4.31 percent by weight, is added to the above reaction vessel while holding pentafluorophenyl magnesium bromide therein under a nitrogen gas flow, and the two substances are stirred and mixed. The temperature of the contents during the mixing (mixing temperature) has risen up to 79.0° C. Then, the resulting reaction solution is subject to reaction for 2 hours with stirring. Consequently, a tetrakis(pentafluorophenyl)borate derivative as the tetrakis(pentafluorophenyl)borate derivative (13) is obtained in the form of a mixed solution of diethyl ether and cyclohexane. A reaction yield of the tetrakis(pentafluorophenyl)borate derivative based on pentafluorophenyl magnesium bromide found in the same manner as Example 13 is 87.7 percent by mole.

EXAMPLE 18

Air inside a reaction vessel of the same kind as the one used in Example 13 is displaced by a nitrogen gas in a satisfactory manner. Then, 1.503 g (0.062 mole) of magnesium, 9.770 g (0.058 mole) of pentafluorobenzene, and 15 ml of diethyl ether are charged to the reaction vessel. Also, 8.169 g (0.063 mole) of isopropyl bromide is charged to the dropping funnel. Next, isopropyl bromide is dropped to the above content with stirring under a nitrogen gas flow. After the completion of the dropping, the resulting reaction solution is subject to reaction for 2 hours at 58.0° C. with stirring. Consequently, pentafluorophenyl magnesium bromide is obtained in the form of a diethyl ether solution. A reaction yield of pentafluorophenyl magnesium bromide found in the same manner as Example 13 is 84.0 percent by mole.

Next, 93.1 g (0.041 mole) of a solution, which is prepared by dissolving tris(pentafluorophenyl)borane into toluene (hydrocarbon solvent) in such a manner that a concentration of tris(pentafluorophenyl)borane is 22.82 percent by weight, is added to the above reaction vessel while holding pentafluorophenyl magnesium bromide under a nitrogen gas flow, and two substances are stirred and mixed. The temperature of the contents during the mixing (mixing temperature) has risen up to 102.0° C. Then, the resulting reaction solution is subject to reaction for 2 hours with stirring. Consequently, a tetrakis(pentafluorophenyl)borate derivative is obtained in the form of a mixed solution of diethyl ether and toluene. A reaction yield of the tetrakis (pentafluorophenyl)borate derivative based on pentafluorophenyl magnesium bromide found in the same manner as Example 13 is 81.5 percent by mole.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing a tetrakis(fluoroaryl)borate derivative expressed by Formula (10):

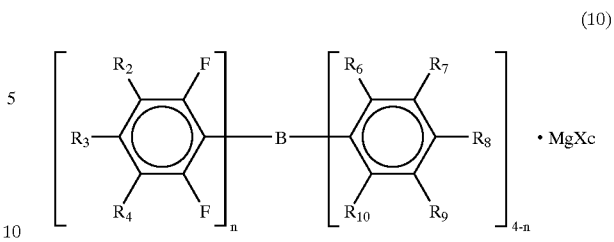

where each of $R_2$–$R_4$ and $R_6$–$R_{10}$ represents one of a hydrogen atom, a fluorine atom, a hydrocarbon group, and an alkoxy group, while at least one of $R_6$–$R_{10}$ represents a fluorine atom, Xc represents one of a chlorine atom, a bromine atom, and an iodine atom, and n represents one of 2 and 3, comprising, (A) reacting an aryl fluoride expressed by Formula (6):

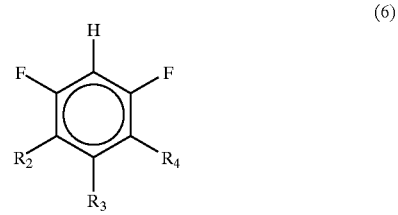

where each of $R_2$–$R_4$ represents one of a hydrogen atom, a fluorine atom, a hydrocarbon group, and an alkoxy group;

halogenated hydrocarbon expressed by Formula (7):

$$R_0 Xa \qquad (7)$$

where $R_0$ represents a hydrocarbon group, and Xa represents one of a chlorine atom, a bromine atom, and an iodine atom; and magnesium with one another in a solvent (a) containing diethyl ether and/or tetrahydrofuran to obtain a reaction mixture containing a fluoroaryl magnesium derivative expressed by Formula 8):

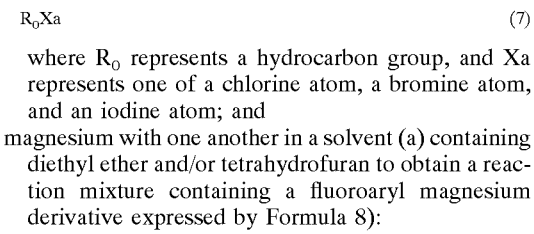

where each of $R_2$–$R_4$ represents one of a hydrogen atom, a fluorine atom, a hydrocarbon group, and an alkoxy group, and Xa represents one of a chlorine atom, a bromine atom, and an iodine atom, said reaction being carried out by mixing said aryl fluoride of Formula (6), said magnesium and solvent (a), and thereafter adding said halogenated hydrocarbon of Formula (7) to a resultant mixture, (B) without isolating said fluoroaryl magnesium derivative (8) from the reaction mixture obtained in (A), reacting said fluoroaryl magnesium derivative (8) with boron halide expressed by Formula (2)

$$BXb_3 \qquad (2)$$

where Xb represents one of a fluorine atom, a chlorine atom, a bromine atom, and an iodine atom, (C) adding a resulting reaction solution to a solvent (b) having a higher boiling point than diethyl ether and/or tetrahydrofuran, (D) distilling out diethyl ether and/or tetrahydrofuran to obtain a (fluoroaryl)borane compound expressed by Formula (9):

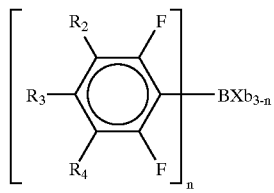

(9)

where each of $R_2$–$R_4$ represents one of a hydrogen atom, a fluorine atom, a hydrocarbon group, and an alkoxy group, Xb represents one of a fluorine atom, a chlorine atom, a bromine atom, and an iodine atom, and n represents one of 2 and 3, and (E) reacting said (fluoroaryl)borane compound with a fluoroaryl magnesium derivative expressed by Formula (4):

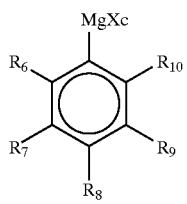

(4)

where each of $R_6$–$R_{10}$ represents one of a hydrogen atom, a fluorine atom, a hydrocarbon group, and an alkoxy group, while at least one of $R_6$–$R_{10}$ represents a fluorine atom, and Xc represents one of a chlorine atom, a bromine atom, and an iodine atom.

2. The process for preparing a tetrakis(fluoroaryl)borate derivative of claim 1, wherein said solvent (b) has a boiling point of 60° C. or above.

3. The process for preparing a tetrakis(fluoroaryl)borate derivative of claim 1, wherein a molar ratio of said halogenated hydrocarbon expressed by Formula (7) to aryl fluoride expressed by Formula (6) is 0.5 or greater.

4. The process for preparing a tetrakis(fluoroaryl)borate derivative of claim 1, wherein a molar ratio of magnesium to aryl fluoride expressed by Formula (6) is 0.5 or greater.

5. The process for preparing a tetrakis(fluoroaryl)borate derivative of claim 1, wherein said halogenated hydrocarbon expressed by Formula (7) and said solvent (a) are mixed with each other in a range between −20° C. and a reflux temperature of said solvent (a) inclusive.

6. The process for preparing a tetrakis(fluoroaryl)borate derivative of claim 1, wherein said aryl fluoride expressed by Formula (6) and said halogenated hydrocarbon expressed by Formula (7) are reacted with each other in a range between 30° C. and a reflux temperature of said solvent (a) inclusive.

7. The process for preparing a tetrakis(fluoroaryl)borate derivative of claim 1, wherein a mole ratio of said fluoroaryl magnesium derivative expressed by Formula (8) to said boron halide expressed by Formula (2) (fluoroaryl magnesium derivative/boron halide) is in a range between 1.0 and 5.0.

8. The process for preparing a tetrakis(fluoroaryl)borate derivative of claim 1, wherein said fluoroaryl magnesium derivative expressed by Formula (8) and said boron halide expressed by Formula (2) are mixed with each other at 80° C. or below.

9. The process for preparing a tetrakis(fluoroaryl)borate derivative of claim 1, wherein said fluoroaryl magnesium derivative expressed by Formula (8) and said boron halide expressed by Formula (2) are reacted with each other in a range between 30° C. and a reflux temperature of said solvent (a) inclusive.

10. A process for preparing a tetrakis(fluoroaryl)borate derivative expressed by Formula (11):

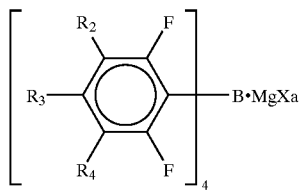

(11)

where each of $R_2$–$R_4$ represents one of a hydrogen atom, a fluorine atom, a hydrocarbon group, and an alkoxy group, and Xa represents one of a chlorine atom, a bromine atom, and an iodine atom, comprising, (A) reacting an aryl fluoride expressed by Formula (6):

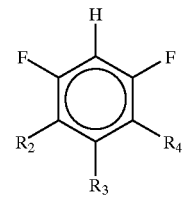

(6)

where each of $R_2$–$R_4$ represents one of a hydrogen atom, a fluorine atom, a hydrocarbon group, and an alkoxy group;

halogenated hydrocarbon expressed by Formula (7):

$R_0Xa$ (7)

where $R_0$ represents a hydrocarbon group, and Xa represents one of a chlorine atom, a bromine atom, and an iodine atom; and magnesium with one another in one of an ether solvent (e) and a mixed solvent of said ether solvent (e) and a hydrocarbon solvent to obtain a reaction mixture containing a fluoroaryl magnesium derivative expressed by Formula (8):

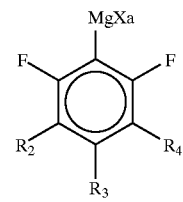

(8)

where each of $R_2$–$R_4$ represents one of a hydrogen atom, a fluorine atom, a hydrocarbon group, and an alkoxy group, and Xa represents one of a chlorine atom, a bromine atom, and an iodine atom, said reaction being carried out by mixing said aryl fluoride expressed by Formula (6), said magnesium and said ether solvent (e) or said mixed solvent, and thereafter adding said halogenated hydrocarbon expressed by Formula (7) to a resultant mixture, and then (B) without isolating said fluoroaryl magnesium derivative (8) from the reaction mixture obtained in (A), reacting said fluoroaryl magnesium derivative (8) with boron halide expressed by Formula (2):

$$BXb_3 \quad (2)$$

where Xb represents one of a fluorine atom, a chlorine atom, a bromine atom, and an iodine atom to obtain said tetrakis(fluoro)borate derivative (11).

11. The process for preparing a tetrakis(fluoroaryl)borate derivative of claim 10, wherein a molar ratio of said halogenated hydrocarbon expressed by Formula (7) to aryl fluoride expressed by Formula (6) is 0.5 or greater.

12. The process for preparing a tetrakis(fluoroaryl)borate derivative of claim 10, wherein a molar ratio of magnesium to aryl fluoride expressed by Formula (6) is 0.5 or greater.

13. The process for preparing a tetrakis(fluoroaryl)borate derivative of claim 10, wherein said fluoroaryl magnesium derivative expressed by Formula (8) and said boron halide expressed by Formula (2) are mixed with each other in a range between −20° C. and a reflux temperature of said solvent (e) or said mixed solvents, whichever is used, inclusive.

14. The process for preparing a tetrakis(fluoroaryl)borate derivative of claim 10, wherein said fluoroaryl magnesium derivative expressed by Formula (8) and said boron halide expressed by Formula (2) are reacted with each other in a range between 30° C. and a reflux temperature of said solvent (e) or said mixed solvent, whichever is used, inclusive.

15. A process for preparing tetrakis(fluoroaryl)borate derivative expressed by Formula (13):

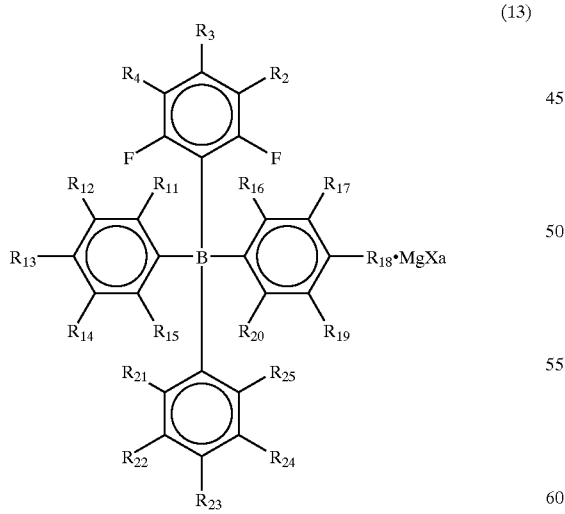

where each of $R_1$–$R_4$ and $R_{11}$–$R_{25}$ represent one of a hydrogen atom, a fluorine atom, a hydrocarbon group and an alkoxy groups while at least one of $R_{11}$–$R_{25}$ represents a fluorine atom, and Xa represents one of a chlorine atom, a bromine atom, and an iodine atom, comprising (A) reacting aryl fluoride expressed by Formula (6):

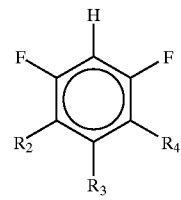

where each of $R_2$–$R_4$ represents one of a hydrogen atom, a fluorine atom, a hydrocarbon group, and an alkoxy group;
halogenated hydrocarbon expressed by Formula (7)

$$R_0 Xa \quad (7)$$

where $R_0$ represents a hydrocarbon group, and Xa represents one of a chlorine atom, a bromine atom, and an iodine atom; and magnesium with one another in one of an ether solvent (e) and a mixed solvent of said ether solvent (e) and a hydrocarbon solvent to obtain a reaction mixture containing a fluoroaryl magnesium derivative expressed by Formula (8):

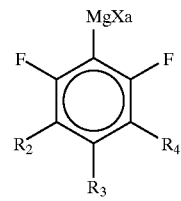

where each of $R_2$–$R_4$ represents one of a hydrogen atom, a fluorine atom, a hydrocarbon group, and an alkoxy group, and Xa represents one of a chlorine atom, a bromine atom, and an iodine atom, said reaction being carried out by mixing said aryl fluoride expressed by Formula (6), said magnesium and said ether solvent (e) or said mixed solvent, and thereafter adding said halogenated hydrocarbon expressed by Formula (7) to a resultant mixture, and then (B) without isolating said fluoroaryl magnesium derivative (8) from the reaction mixture obtained in (A), reacting said fluoroaryl magnesium derivative (8) with tris(fluoroaryl)borane expressed by Formula (12):

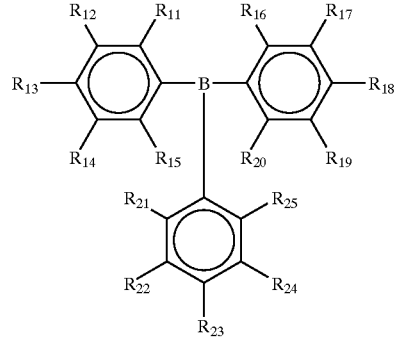

where each of $R_{11}$–$R_{25}$ represents one of a hydrogen atom, a fluorine atom, a hydrocarbon group, and an alkoxy group, while at least one of $R_{11}$–$R_{25}$ represents a fluorine atom to obtain said tetrakis(fluoroaryl)borate derivative (13).

16. The process for preparing a tetrakis(fluoroaryl)borate derivative of claim 15, wherein a molar ratio of said halogenated hydrocarbon expressed by Formula (7) to said aryl fluoride expressed by Formula (6) is 0.5 or greater.

17. The process for preparing a tetrakis(fluoroaryl)borate derivative of claim 15, wherein a molar ratio of magnesium to said aryl fluoride expressed by Formula (6) is 0.5 or greater.

18. The process for preparing a tetrakis(fluoroaryl)borate derivative of claim 15, wherein said fluoroaryl magnesium derivative expressed by Formula (8) and said tris(fluoroaryl) borane expressed by Formula (12) are mixed with each other in a range between −20° C. and a reflux temperature of said solvent (e) or said mixed solvents whichever is used, inclusive.

19. The process for preparing tetrakis(fluoroaryl)borate derivative of claim 15, wherein said fluoroaryl magnesium derivative expressed by Formula (8) and said tris(fluoroaryl) borane expressed by Formula (12) are reacted with each other in a range between 30° C. and a reflux temperature of said solvent (e) or said mixed solvent, whichever is used, inclusive.

* * * * *